United States Patent [19]

Wrobleski et al.

[11] Patent Number: 4,567,158

[45] Date of Patent: Jan. 28, 1986

[54] PROCESS FOR PREPARING PHOSPHORUS-VANADIUM MIXED OXIDE OXIDATION CATALYSTS

[75] Inventors: James T. Wrobleski, St. Louis; James W. Edwards, Creve Coeur; Charles R. Graham, St. Charles; Robert A. Keppel, St. Louis; Harold Raffelson, Olivette, all of Mo.

[73] Assignee: Monsanto Company, St. Louis, Mo.

[21] Appl. No.: 566,361

[22] Filed: Dec. 28, 1983

[51] Int. Cl.$^4$ .................... B01J 27/14; C07D 307/34
[52] U.S. Cl. ..................................... 502/209; 549/259
[58] Field of Search ........................................ 502/209

[56] References Cited

U.S. PATENT DOCUMENTS

| | | | |
|---|---|---|---|
| 3,864,280 | 2/1975 | Schneider | 252/435 |
| 4,132,670 | 1/1979 | Katsumoto et al. | 252/437 |
| 4,149,992 | 4/1979 | Mount et al. | 502/209 |
| 4,187,235 | 2/1980 | Katsumoto et al. | 260/346.75 |
| 4,251,390 | 2/1981 | Barone | 252/435 |
| 4,253,988 | 3/1981 | Mount et al. | 502/209 |
| 4,293,498 | 10/1981 | Lemanski et al. | 260/346.75 |
| 4,294,722 | 10/1981 | Bremer et al. | 252/435 |
| 4,312,787 | 1/1982 | Dolkyj et al. | 252/435 |
| 4,315,864 | 2/1982 | Bremer et al. | 260/346.75 |
| 4,333,853 | 6/1982 | Millberger et al. | 502/209 |
| 4,350,611 | 9/1982 | Lemanski et al. | 502/209 |
| 4,350,639 | 9/1982 | Millberger et al. | 549/259 |
| 4,359,405 | 11/1982 | Mount et al. | 502/209 |
| 4,361,501 | 11/1982 | Blum et al. | 502/209 |
| 4,365,069 | 12/1982 | Bremer et al. | 502/209 |
| 4,374,043 | 2/1983 | Blum et al. | 502/209 |
| 4,392,986 | 7/1983 | Yang et al. | 502/209 |
| 4,412,940 | 11/1983 | Mount et al. | 502/209 |
| 4,435,521 | 3/1984 | Yang et al. | 502/209 |

FOREIGN PATENT DOCUMENTS 2727617 12/1977 Fed. Rep. of Germany ...... 502/209

*Primary Examiner*—John Doll
*Assistant Examiner*—William G. Wright
*Attorney, Agent, or Firm*—Wendell W. Brooks; James C. Logomasini; Arnold H. Cole

[57] ABSTRACT

Phosphorus-vanadium mixed oxide oxidation catalysts are prepared by introducing a substantially pentavalent vanadium-containing compound and a pentavalent phosphorus-containing compound into an alcohol medium capable of reducing the vanadium to a valence state less than +5 in the presence of an alcohol-modifying agent to form a phosphorus-vanadium mixed oxide catalyst precursor. The catalyst precursor is recovered, dried, formed into desired structures, and calcined at temperatures from about 250° C. to about 600° C. The catalysts are highly effective in that they exhibit a weight/weight productivity of at least 70 grams of maleic anhydride per kilogram of catalyst per hour.

66 Claims, 18 Drawing Figures

PROCESS FOR PREPARING PHOSPHORUS-VANADIUM MIXED OXIDE OXIDATION CATALYSTS

BACKGROUND OF THE INVENTION

1. Field of the Invention

This invention relates to a process for the preparation of phosphorus-vanadium mixed oxide oxidation catalysts. More particularly, this invention relates to a process for the preparation of phosphorus-vanadium mixed oxide oxidation catalysts useful for the partial oxidation of non-aromatic hydrocarbons in the vapor phase with molecular oxygen or a molecular oxygen-containing gas to produce maleic anhydride in excellent yields, the catalyst exhibiting a single pass weight/weight productivity of at least 70 grams of maleic anhydride per kilogram of catalyst per hour.

Maleic anhydride is of significant commercial interest throughout the world. It is used alone or in combination with other acids in the manufacture of alkyd and polyester resins. It is also a versatile intermediate for chemical synthesis. Significant quantities of maleic anhydride are produced each year to satisfy these varied needs.

2. Description of the Prior Art

Numerous catalysts containing mixed oxides of phosphorus and vanadium are disclosed in the prior art as being useful for the conversion of various organic feedstocks to maleic anhydride, and further that such catalysts wherein the valence of the vanadium is between about +3.8 and +4.8 are particularly well suited for the production of maleic anhydride from saturated hydrocarbons having at least four carbon atoms in a straight chain. In many instances, these catalysts also contain added promoter elements which are considered to exist in the catalysts as the oxide. Common organic feedstocks include non-aromatic hydrocarbons such as n-butane, 1- and 2-butenes, 1,3-butadiene, or mixtures thereof.

Procedures for the preparation of catalysts containing the mixed oxides of phosphorus and vanadium are also disclosed and taught by the prior art. Many of such procedures teach that it is preferable to reduce the vanadium in solution to the tetravalent state. For example, these catalysts can be prepared by contacting phosphorus compounds and vanadium compounds under conditions sufficient to produce the tetravalent vanadium and to form the catalyst precursor. The catalyst precursor is thereafter recovered, dried, and calcined to produce the active catalyst.

U.S. Pat. No. 4,333,853 discloses a phosphorus-vanadium mixed oxide catalyst prepared by reducing vanadium substantially in the pentavalent valence state to a tetravalent valence state in the presence of a phosphorus-containing compound and in the absence of a corrosive reducing agent in an organic liquid medium capable of reducing the vanadium to a valence state less than +5, recovering the resulting vanadium-phosphorus mixed oxide catalyst precursor, drying such precursor, and calcining the precursor to obtain the active catalyst. Such catalysts reportedly are effective in the oxidation of C4 hydrocarbons such as n-butane, n-butenes (1- and 2-butenes), 1,3-butadiene, or mixtures thereof to produce maleic anhydride with selectivities ranging from 58.7% to 68.1% and yields (mole %) ranging from 51.4% to 59.5%.

U.S. Pat. No. 4,315,864 relates to a process for the production of maleic anhydride from C4 hydrocarbons in the presence of a phosphorus-vanadium mixed oxide catalyst. The catalyst is prepared by reducing a pentavalent vanadium-containing compound in an olefinic, oxygenated organic liquid medium to a +4 valence in the absence of a corrosive reducing agent, recovering the resultant catalyst precursor, drying the catalyst precursor, and calcining the precursor to obtain the active catalyst.

U.S. Pat. No. 4,312,787 describes a catalyst which comprises an inert support and a catalytically active mixed oxide material coating of phosphorus and vanadium or of phosphorus, vanadium, and uranium on the outer surface of the support in an amount greater than 50% to about 80% by weight of the combined support and oxide material. Catalysts within the scope of the claims of the patent were reported to produce maleic anhydride from n-butane in yields ranging from 53% to 62.5%, with selectivities ranging from 57.4% to 67.9%.

U.S. Pat. No. 4,294,722 discloses a process for preparing catalysts containing mixed oxides of phosphorus and vanadium. In this process, a pentavalent vanadium-containing compound is reduced (at least in part) to a +4 valence state in an organic liquid medium in which the vanadium compound is at least partially soluble to form a solution or mixture. Any unsolubilized vanadium-containing compound having a particle size greater than 0.1 mm diameter is removed. The resulting solution is mixed with a pentavalent phosphorus-containing compound to form a precipitate which is recovered, dried, and calcined. Such catalysts are reported to be effective in the oxidation of non-branched C4 hydrocarbons, such as n-butane, 1- and 2-butenes, 1,3-butadiene, and mixtures thereof, in the presence of molecular oxygen or a molecular oxygen-containing gas in the vapor phase to maleic anhydride with good selectivity.

U.S. Pat. No. 4,293,498 discloses a process for preparing phosphorus-vanadium mixed oxide catalysts. In this process, a pentavalent vanadium-containing compound is reduced to a +4 valence state in an olefinic, halogenated organic liquid-containing medium either in the presence or absence of a phosphorus-containing compound. The resulting catalyst precursor is recovered, dried, and calcined to produce the active catalyst. Such catalysts reportedly are effective in the oxidation of non-branched C4 hydrocarbons, such as n-butane, 1- and 2-butenes, 1,3-butadiene, and mixtures thereof, in the presence of molecular oxygen or a molecular oxygen-containing gas in the vapor phase to produce maleic anhydride in high yields and good selectivities.

In U.S. Pat. No. 4,187,235, a process is described for preparing maleic anhydride from n-butane in the presence of a phosphorus-vanadium oxygen high surface area catalyst, that is, 10 to 100 square meters per gram (BET method). The catalyst is prepared by reducing pentavalent vanadium to a valence between +4.0 and +4.6 with a substantially anhydrous primary or secondary alcohol and contacting the reduced vanadium with phosphoric acid, followed by recovering and calcining the resulting vanadium (IV) phosphate compound.

In U.S. Pat. No. 4,251,390, a zinc-promoted phosphorus-vanadium-oxygen catalyst is disclosed and claimed. The catalyst is prepared by reducing pentavalent vanadium in a substantially anhydrous organic medium to a lower valence state and digesting the reduced vanadium in the presence of a zinc promoter compound. The resulting catalyst is activated by bringing the catalyst to operating temperatures for the oxidation of n-butane to maleic anhydride at a rate of 5° C. to 10° C. per hour in the presence of a butane-in-air mixture.

U.S. Pat. No. 4,132,670 discloses a process for preparing a crystalline vanadium (IV) phosphate catalyst composition having a surface area in excess of 10 square meters per gram. In this process, orthophosphoric acid is reacted with a vanadium (IV) oxycompound by contacting a suspension of the vanadium compound in a hydroxylic organic medium, for example, isobutyl alcohol, with the phosphoric acid at a temperature in the range of 20° C. and 210° C. until the conversion is completed. The resulting catalyst is activated by heating at elevated temperatures in a butane-in-air mixture.

U.S. Pat. No. 3,864,280 discloses phosphorus-vanadium mixed oxide catalysts having an intrinsic surface area from about 7 to about 50 square meters per gram. The catalysts are prepared by precipitation of a phosphorus-vanadium-oxygen complex from an essentially organic solvent medium in the absence of gross amounts of water. The resulting crystalline precipitate is activated by heating in air followed by a 1.5 mole percent butane-in-air mixture, both at elevated temperatures.

Although these prior art processes generally are effective to provide the desired catalyst, the commercial utility of a catalyst system and a catalytic process is highly dependent upon the cost of the catalyst employed, the conversion of the reactants and the yield of the desired product(s), or stated differently, the actual productivity of the catalyst system. In many instances, a reduction in the cost of a catalyst system employed in a given process on the order of a few cents per kilogram or pound, or a small percent increase in the yield of the desired product, relative to the amount of catalyst required, represents a tremendous commercial economical savings and advantage. Accordingly, research efforts are continually being made to define new or improved catalyst systems and methods and processes of making new and old catalyst systems to reduce the cost and/or upgrade the activity, selectivity, and/or productivity of such catalyst systems in such processes. The discovery of the process of the instant invention, therefore, is believed to be a decided advance in the catalyst art.

SUMMARY OF THE INVENTION

Figure 1:
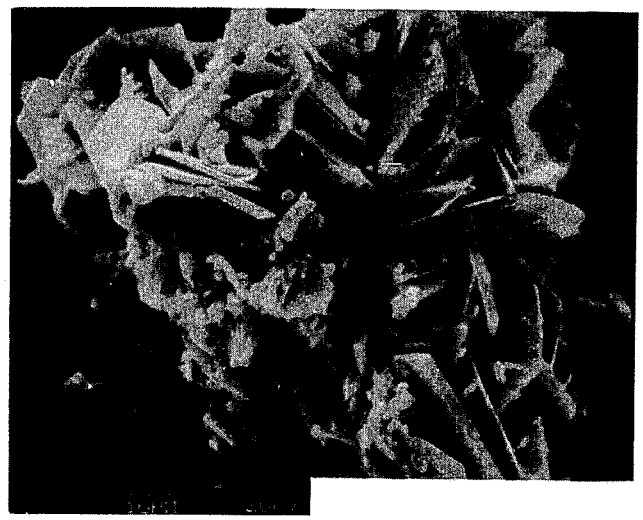
FIG. 1 is a scanning electron micrograph of phosphorus-vanadium mixed oxide catalyst precursor particles, prepared by HCl reduction of $V_2O_5$ in water and contacting the same with $H_3PO_4$, and which was heated at 365° C. for two hours, at a 2,000X magnification.

It is an object of this invention to provide a process for preparing a phosphorus-vanadium mixed oxide catalyst useful for the oxidation of non-aromatic hydrocarbons to produce maleic anhydride.

Another object of this invention is to provide a process for preparing a phosphorus-vanadium mixed oxide catalyst useful for the oxidation of non-aromatic hydrocarbons, which catalysts exhibit excellent weight/weight productivity, yields, and selectivities to maleic anhydride.

To achieve these and other objects, together with the advantages thereof, which will become apparent from the accompanying description and claims, a process is provided which comprises:

(a) introducing a substantially pentavalent vanadium-containing compound into an alcohol medium capable of reducing the vanadium to a valence state less than +5 to form a slurry;

(b) contacting the slurry with an effective amount of an alcohol modifying agent;

(c) effecting the reduction of at least a portion of the vanadium to a valence state of +4;

(d) adding a pentavalent phosphorus-containing compound to the vanadium-containing mixture before or after effecting the reduction to form a phosphorus-vanadium mixed oxide catalyst precursor;

(e) recovering the phosphorus-vanadium mixed oxide catalyst precursor;

(f) drying the catalyst precursor; and (g) calcining the catalyst precursor at a temperature from about 250° C. to about 600° C., wherein the catalysts exhibit a weight/weight productivity to maleic anhydride of at least 70 grams of maleic anhydride per kilogram of catalyst per hour.

DESCRIPTION OF THE PREFERRED EMBODIMENTS

In accordance with this invention, a process is provided for the preparation of phosphorus-vanadium mixed oxide catalysts which are useful for the partial oxidation of non-aromatic hydrocarbons having at least four carbon atoms in a straight chain with molecular oxygen or a molecular oxygen-containing gas in the vapor phase to maleic anhydride. These catalysts, exhibit a weight/weight productivity to maleic anhydride of at least 70 grams of maleic anhydride per kilogram of catalyst per hour.

For purposes of this invention, the term "weight/weight productivity" means the weight of maleic anhydride (MAN) expressed in grams produced during a single pass of hydrocarbon feedstock over the catalyst per unit weight of the catalyst expressed in kilograms per unit of time expressed in hours, the term expressed as g maleic anhydride/kg catalyst-hour or g MAN/kg cat.-hr. The term "yield" means the ratio of the moles of maleic anhydride obtained to the moles of hydrocarbon feedstock introduced into the reactor. The term "selectivity" means the ratio of moles of maleic anhydride obtained to the moles of hydrocarbon feedstock reacted or converted multiplied by 100, the term expressed as mole percent. The term "conversion" means the ratio of the moles of hydrocarbon feedstock reacted to the moles of hydrocarbon introduced into the reactor multiplied by 100, the term expressed as mole percent. The term "space velocity" or "gas hourly space velocity" or "GHSV" means the hourly volume of gaseous feed expressed in cubic centimeters (cc) at 20° C. and atmospheric pressure, divided by the catalyst bulk volume, expressed in cubic centimeters, the term expressed as cc/cc/hour or hr⁻¹.

Component source materials suitable for use in the process of the instant invention are those which yield the unique phosphorus-vanadium mixed oxdie catalysts which, according to the instant process, are sufficiently active and selective to provide a weight/weight productivity of at least 70 g MAN/kg cat.-hr. The vanadium compounds useful as a source of vanadium in the catalysts prepared in accordance with the instant process in general are those containing pentavalent vanadium and includes vanadium pentoxide or vanadium salts, such as ammonium metavanadate and vanadium oxytrihalides. Among these compounds, vanadium pentoxide is preferred.

The phosphorus compounds useful as a source of phosphorus in the catalysts prepared in accordance with the instant process are preferably those which contain pentavalent phosphorus. Suitable phosphorus compounds containing pentavalent phosphorus include phosphoric acid, phosphorus pentoxide, or phosphorus perhalides, such as phosphorus pentachloride. Of these phosphorus-containing compounds, phosphoric acid and phosphorus pentoxide are preferred.

In accordance with the instant process, the catalysts are normally prepared by introducing a substantially pentavalent vanadium-containing compound and a pentavalent phosphorus-containing compound into an alcohol medium capable of reducing the vanadium to a valence state less than +5 to form a slurry.

The resultant slurry is contacted with an effective amount of an alcohol-modifying agent capable of modifying the alcohol to a state conducive to the formation of the catalyst precursor. It will be noted that the exact function and mode of action of the alcohol-modifying agent is not completely understood. While not desiring to be bound by theory of the invention or to limit the invention in any way, it is believed that the alcohol-modifying agent alters the surface tension of the alcohol to enhance intimate contact among the phosphorus-containing compound, the vanadium-containing compound, promoter element-containing compounds (when present), and the alcohol, and thereby promotes the formation of the highly porous catalyst precursor which is convertible to the catalyst of the instant invention. Suitable, but nonlimiting, alcohol-modifying agents include hydrogen iodide, sulfur dioxide, fuming sulfuric acid, and surfactants, such as those described in U.S. Pat. No. 4,149,992, which specification is herein incorporated by reference.

The amount of alcohol-modifying agent employed is not narrowly critical. All that is necessary, as previously noted, is that an amount sufficient to modify the alcohol to a state conducive to the formation of the catalyst precursor be employed. An amount sufficient to provide a alcohol-modifying agent/vanadium-containing compound mole ratio of 1.0 is normally employed. Larger or smaller amounts may, however, be employed, if desired.

The phosphorus-containing compound may be introduced into the vanadium/alcohol/alcohol-modifying agent mixture in any convenient manner. It may be added in the form of a solution or suspension in the alcohol medium or component of the mixture or when the phosphorus-containing compound is in liquid form, such as $\geq 100\%$ phosphoric acid, it may be added alone. Alternatively, a vanadium-containing compound and a phosphorus-containing compound, such as $\geq 100\%$ phosphoric acid may be introduced simultaneously into the alcohol medium. In yet another mode, the vanadium-containing compound is introduced into a solvent or dispersion of the phosphorus-containing compound in the alcohol. It is preferred, however, to introduce the phosphorus-containing compound to effectuate contacting of the phosphorus-containing compound and the vanadium-containing compound by introducing the phosphorus-containing compound to a mixture of the vanadium-containing compound, the alcohol, and the alcohol-modifying agent.

The alcohols employed during the preparation of the catalysts in accordance with the instant process are preferably anhydrous and must be capable of reducing at least a portion of the vanadium to a +4 valence state, either upon addition of the vanadium compound or upon mixing and heating. In addition, the alcohol should be a solvent for the phosphorus-containing compound, especially the preferred phosphoric acid, and be relatively unreactive toward such phosphorus-containing compound. Preferably, however, the alcohol is not a solvent for the catalyst precursor mixed oxides of phosphorus and vanadium. In those instances wherein the catalyst precursor is soluble in the alcohol medium, precipitation should be easily induced by removal of a portion of the alcohol. Suitable alcohols include primary and secondary alcohol, such as methanol, ethanol, 1-propanol, 2-propanol, 1-butanol, 2-methyl-1-propanol (isobutyl alcohol), 3-methyl-2-butanol, 2,2-dimethyl-1-propanol, 1,2-ethanediol (ethylene glycol). Of these alcohols, isobutyl alcohol is preferred.

After the phosphorus and vanadium compounds are introduced into the alcohol medium to form the vanadium compound/phosphorus compound/alcohol/alcohol-modifying agent mixture, reduction of at least a portion of the vanadium to a valence state of +4 is effected, preferably by heating the mixture, with stirring, if desired, until a blue solution or slurry is obtained. In general, heating the mixture at reflux temperatures for a period of time ranging from about four hours to about 20 hours is sufficient.

During the course of carrying out the vanadium reduction, the catalyst precursor forms. In most instances, the precursor precipitates from the alcohol medium as a finely divided precipitate. When hydrogen iodide is employed as the alcohol-modifying agent, however, a homogeneous solution is obtained. That is, the alcohol solubilizes the catalyst precursor. In such instances, it is necessary to remove a portion of the alcohol to induce precipitation of the catalyst; precursor. The precursor precipitate is recovered by conventional techniques well known to those skilled in the art, including filtration, and centrifugation and decantation. The resulting precursor precipitate, when dried, has a free flowing powdery consistency in contrast to the caked residue normally obtained when the catalyst precursor is recovered by gentle heating to dryness.

The phosphorus-vanadium mixed-oxide catalysts prepared in accordance with the instant process contain vanadium in the average valence state of about +3.9 to about +4.6 or simply about 3.9 to about 4.6. This average valence state is achieved when at least a portion of the pentavalent vanadium introduced into the reaction mixture is reduced to the +4 valence state. It is believed that as this reduction occurs, the reduced vanadium simultaneously reacts with the phosphorus present in the reaction mixture to form the phosphorus-vanadium mixed oxide catalyst precursor.

The recovered catalyst precursor is then dried, formed into structures if structures are desired, and calcined at a temperature of about 250° C. to about 600° C. Two basic modes of calcination may be employed. For convenience, these may be referred to as (1) air calcination, and (2) nitrogen/steam calcination.

In the air calcination mode, the catalyst precursors are subjected to calcination temperatures in the presence of air. And in one embodiment, the catalyst precursors are calcined by heating to 400° C. over a two-hour period, maintaining this temperature over an additional six-hour period, and purging the calcination furnace with dry air at the third hour of the heat up/temperature maintenance or hold period, the embodiment conveniently designated as 2(400)6 calcination. In the nitrogen/steam calcination mode, the catalyst precursors are first calcined in air at about 325° C. to about 350° C. for about six hours, followed by calcination in a flowing stream of nitrogen and molecular oxygen-free steam (water) at a temperature from about 250° C. to about 600° C. for two hours to about 10 hours, preferably about 275° C. to about 425° C. for about five hours.

Of these two modes of calcination, the nitrogen/steam calcination is generally preferred in that more active and selective catalysts result which exhibit increased weight/weight productivity.

The catalysts prepared in accordance with the instant process, as previously indicated, are highly active and selective and exhibit increased weight/weight productivity for the production of maleic anhydride from non-aromatic hydrocarbons at relatively mild conditions. This is believed to result from the highly ordered and uniform spheroidal macrostructure of the catalysts.

The characteristic highly ordered and uniform macrostructure of the catalysts of the instant process are evidenced by the surface textural characteristics exhibited in FIGS. 1–18, which are scanning electron micrographs of phosphorus-vanadium mixed oxide catalyst precursors and catalysts known to the prior art and the phosphorus-vanadium mixed oxide catalyst precursors and catalysts of the instant invention.

The micrographs of FIGS. 1–18 were prepared according to standard scanning electron microscopic techniques. In each instance, the sample particles were sprinkled on a support stud which had been coated with silver polish. The samples were then gold coated to render them conductive in order to prevent charging. The samples were examined by a Cambridge Stereoscan S250 scanning electron microscope.

Figure 2:
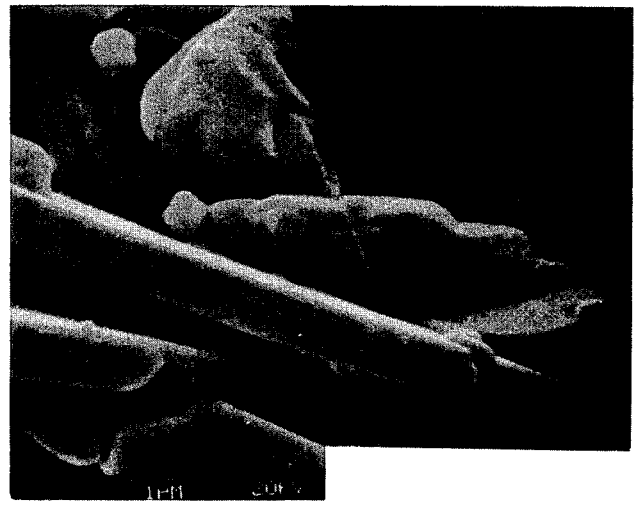
FIG. 2 is a scanning electron micrograph of phosphorus-vanadium mixed oxide catalyst precursor particles, prepared by HCl reduction of $V_2O_5$ in water and contacting the same with $H_3PO_4$, and which was heated at 365° C. for two hours, at a 20,000X magnification.

FIGS. 1 and 2 are scanning electron micrographs of phosphorus-vanadium mixed oxide catalyst precursor particles prepared by HCl reduction of $V_2O_5$ in water and contacting the same with 85.7% $H_3PO_4$, followed by heat treatment at 365° C. for two hours, at 2,000X and 20,000X magnification, respectively. The catalyst precursor is recovered from solution by evaporating to dryness. The general macrostructure of the precursor is that of non-uniform randomly associated platelets.

Figure 3:
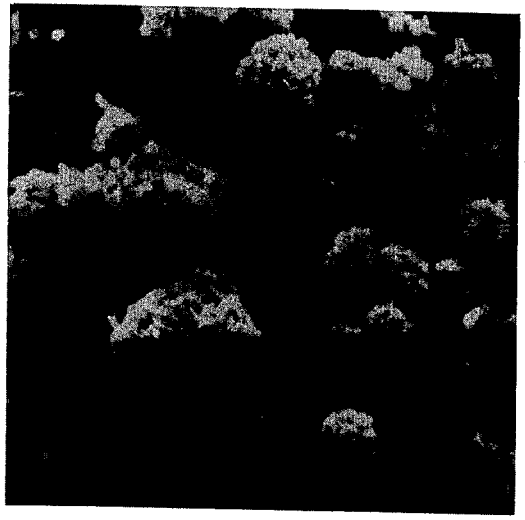
FIG. 3 is a scanning electron micrograph of phosphorus-vanadium mixed oxide catalyst particles prepared by $H_3PO_3$ reduction of $V_2O_5$ in water in the presence of $H_3PO_4$, and which were calcined in dry air at 400° C. for six hours, at a 2,000X magnification.
Figure 4:
FIG. 4 is a scanning electron micrograph of phosphorus-vanadium mixed oxide catalyst particles prepared by $H_3PO_3$ reduction of $V_2O_5$ in water in the presence of $H_3PO_4$, and which were calcined in dry air at 400° C. for six hours, at a 20,000X magnification.

FIGS. 3 and 4 are scanning electron micrographs of phosphorus-vanadium mixed oxide catalyst particles prepared by phosphorous acid ($H_3PO_3$) reduction of $V_2O_5$ in water in the presence of 85% $H_3PO_4$ and calcination in dry air at 400° C. for six hours, at 2,000X and 20,000X magnification, respectively. The catalysts appear to consist of a number of associated platelets.

Figure 5:
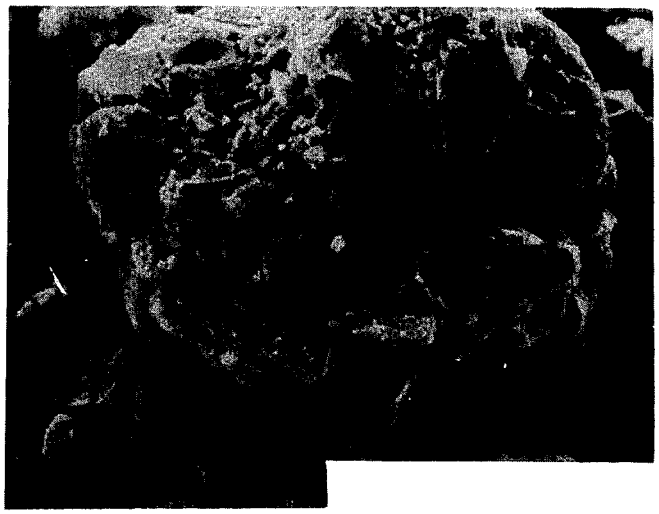
FIG. 5 is a scanning electron micrograph of phosphorus-vanadium mixed oxide catalyst precursor particles under substantially anhydrous conditions by HCl reduction of $V_2O_5$ in isobutyl alcohol and contacting the same with $H_3PO_4$, at a 2,000X magnification.
Figure 6:
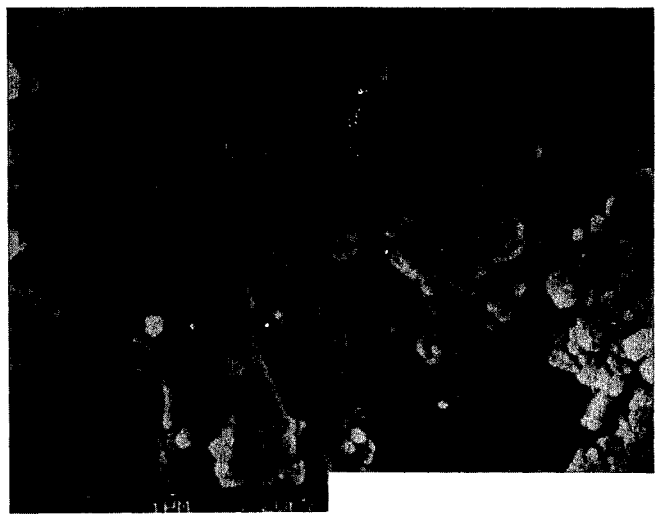
FIG. 6 is a scanning electron micrograph of phosphorus-vanadium mixed oxide catalyst precursor particles, prepared under substantially anhydrous conditions by HCl reduction of $V_2O_5$ in isobutyl alcohol and contacting the same with $H_3PO_4$, at a 20,000X magnification.
Figure 7:
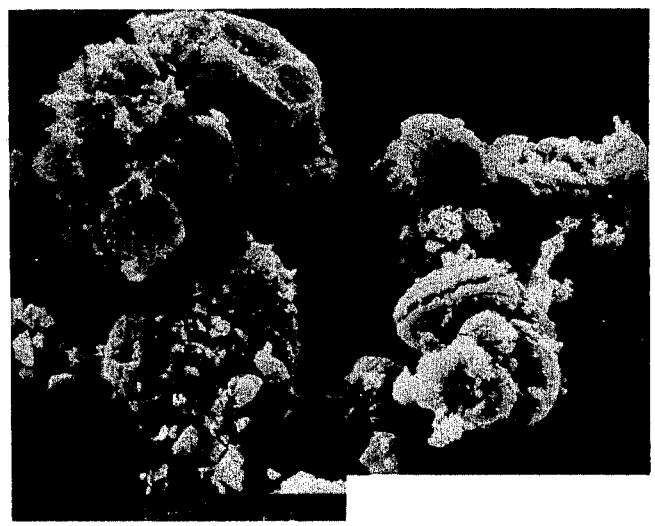
FIG. 7 is a scanning electron micrograph of lithium- and zinc-promoted phosphorus-vanadium mixed oxide catalyst precursor particles, prepared under substantially anhydrous conditions by HCl reduction of $V_2O_5$ in isobutyl alcohol and contacting the same with $H_3PO_4$, and which were heated at 260° C. for three hours, at a 2,000X magnification.
Figure 8:
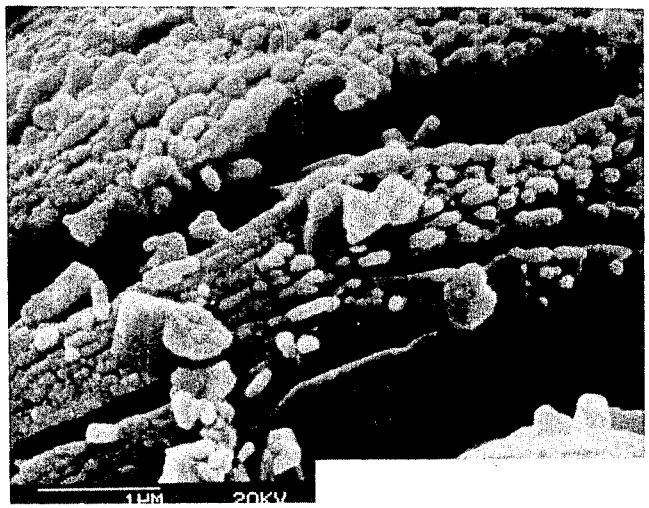
FIG. 8 is a scanning electron micrograph of lithium- and zinc-promoted phosphorus-vanadium mixed oxide catalyst precursor particles, prepared under substantially anhydrous conditions by HCl reduction of $V_2O_5$ in isobutyl alcohol and contacting the same with $H_3PO_4$, and which were heated at 260° C. for three hours, at a 20,000X magnification.
Figure 9:
FIG. 9 is a scanning electron micrograph of lithium- and zinc-promoted phosphorus-vanadium mixed oxide catalyst particles, prepared under substantially anhydrous conditions by HCl reduction of $V_2O_5$ in isobutyl alcohol and contacting the same with $H_3PO_4$, and which were heated at 260° C. for three hours and conditioned by a slow heat up to 400° C. at a rate of 5° C. to 10° C. per hour while adjusting the gas flow from 0.5 to 1.0 mole percent n-butane-in-air at an initial space velocity of 900 hr$^{-1}$ up to 2500 hr$^{-1}$ to maintain a conversion level between 78 mole percent and 80 mole percent, at a 2,000X magnification.
Figure 10:
FIG. 10 is a scanning electron micrograph of lithium- and zinc-promoted phosphorus-vanadium mixed oxide catalyst particles, prepared under substantially anhydrous conditions by HCl reduction of $V_2O_5$ in isobutyl alcohol and contacting the same with $H_3PO_4$, and which were heated at 260° C. for three hours and conditioned by a slow heat up to 400° C. at a rate of 5° C. to 10° C. per hour while adjusting the gas flow from 0.5 to 1.0 mole percent n-butane-in-air at an initial space velocity of 900 hr$^{-1}$ up to 2500 hr$^{-1}$ to maintain a conversion level between 78 mole percent and 80 mole percent, at 20,000X magnification.

FIGS. 5 and 6 are scanning electron micrographs of phosphorus-vanadium mixed oxide catalyst precursor particles, prepared under substantially anhydrous conditions by HCl reduction of $V_2O_5$ in isobutyl alcohol prior to contacting the same with $H_3PO_4$ at 2,000X and 20,000X magnification, respectively. The precursors appear to be relatively non-porous.

FIGS. 7–10 are scanning electron micrographs of lithium- and zinc-promoted phosphorus-vanadium mixed oxide catalyst precursor and catalyst particles prepared under substantially anhydrous conditions by HCl reduction of $V_2O_5$ in isobutyl alcohol prior to contacting same with $H_3PO_4$, at 2,000X and 20,000X magnification. The general macrostructure appears to be that of striated spherical particles composed of a succession of layers stacked one upon the other.

Figure 11:
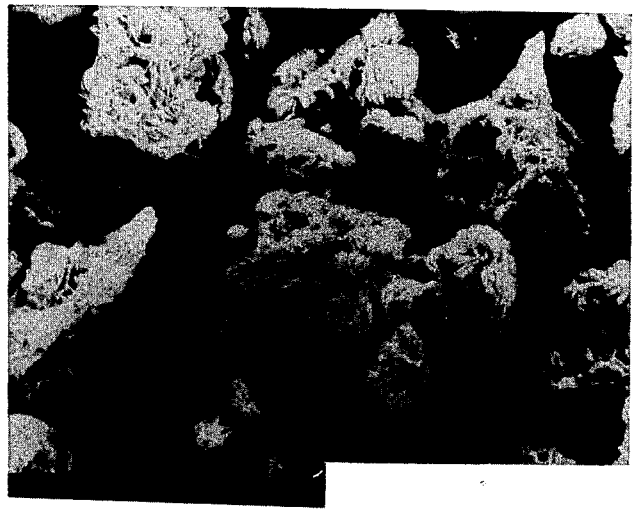
FIG. 11 is a scanning electron micrograph of phosphorus-vanadium mixed oxide catalyst particles, prepared under substantially anhydrous conditions by reduction of $V_2O_5$ in isobutyl alcohol in the presence of $H_3PO_4$ and in the absence of a corrosive reducing agent, and which were calcined in dry air at 400° C. for one hour, at 2,000X magnification.
Figure 12:
FIG. 12 is a scanning electron micrograph of phosphorus-vanadium mixed oxide catalyst particles, prepared under substantially anhydrous conditions by reduction of $V_2O_5$ in isobutyl alcohol in the presence of $H_3PO_4$ and in the absence of a corrosive reducing agent, and which were calcined in dry air at 400° C. for one hour, at 20,000X magnification.
Figure 13:
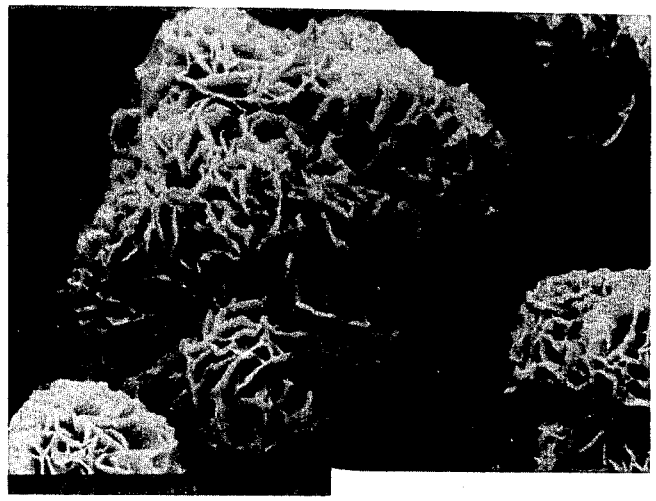
FIG. 13 is a scanning electron micrograph of phosphorus-vanadium mixed oxide catalyst precursor particles of the instant invention, prepared under substantially anhydrous conditions by reduction of $V_2O_5$ in isobutyl alcohol in the presence of $SO_2$ as an alcohol-modifying agent and contacting the same with H₃PO₄, at a 2,000X magnification.
Figure 14:
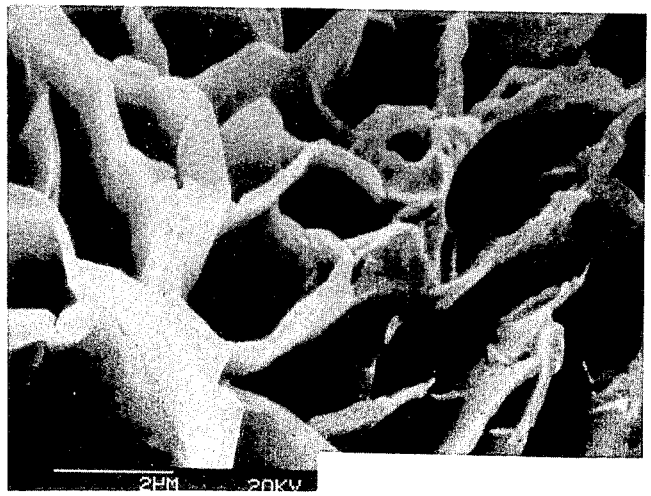
FIG. 14 is a scanning electron micrograph of phosphorus-vanadium mixed oxide catalyst precursor particles of the instant invention, prepared under substantially anhydrous conditions by reduction of $V_2O_5$ in isobutyl alcohol in the presence of $SO_2$ as an alcohol-modifying agent and contacting the same with $H_3PO_4$, at a 20,000X magnification.
Figure 15:
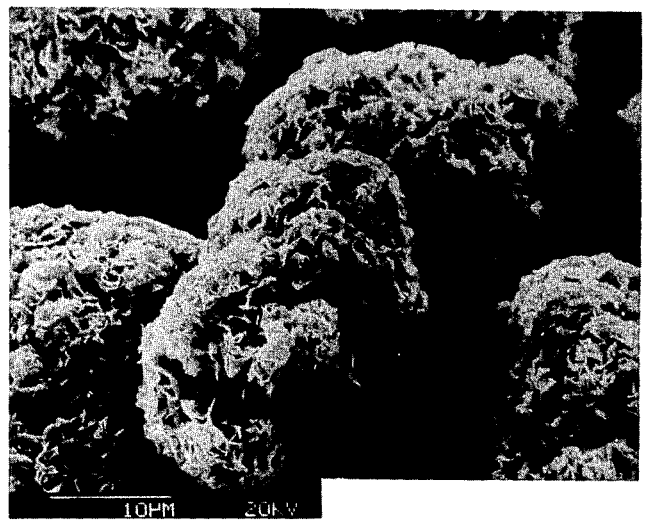
FIG. 15 is a scanning electron micrograph of phosphorus-vanadium mixed oxide catalyst particles of the instant invention, prepared under substantially anhydrous conditions by reduction of $V_2O_5$ in isobutyl alcohol in the presence of $SO_2$ as an alcohol-modifying agent and contacting the same with $H_2PO_4$, and which were calcined in dry air at 350° C. for six hours, at 2,000X magnification.
Figure 16:
FIG. 16 is a scanning electron micrograph of phosphorus-vanadium mixed oxide catalyst particles of the instant invention, prepared under substantially anhydrous conditions by reduction of $V_2O_5$ in isobutyl alcohol in the presence of $SO_2$ as an alcohol-modifying agent and contacting the same with $H_3PO_4$, and which were calcined in dry air at 350° C. for six hours, at 20,000X magnification.
Figure 17:
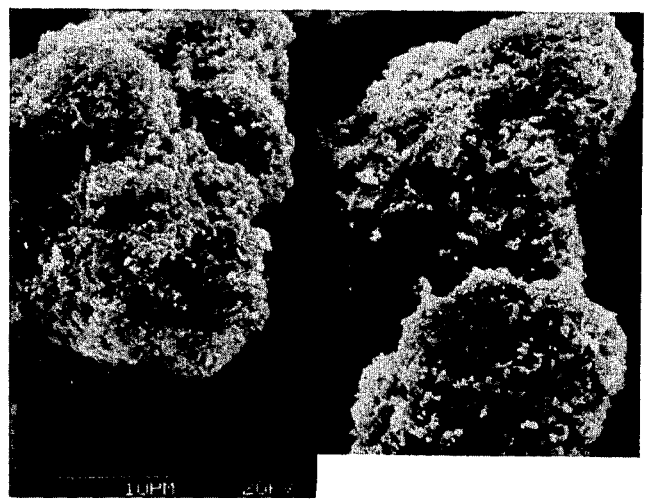
FIG. 17 is a scanning electron micrograph of phosphorus-vanadium mixed oxide catalyst particles of the instant invention, prepared under substantially anhydrous conditions by reduction of $V_2O_5$ in isobutyl alcohol in the presence of $SO_2$ as an alcohol-modifying agent and contacting the same with $H_3PO_4$, and which were calcined in dry air at 350° C. for six hours and subsequently calcined under a nitrogen/steam atmosphere at 415° C. for five hours, at 2,000X magnification.
Figure 18:
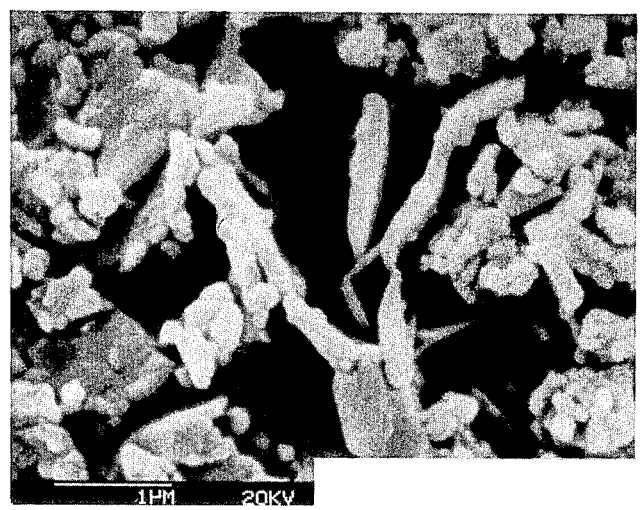
FIG. 18 is a scanning electron micrograph of phosphorus-vanadium mixed oxide catalyst particles of the instant invention, prepared under substantially anhydrous conditions by reduction of $V_2O_5$ in isobutyl alcohol in the presence of $SO_2$ as an alcohol-modifying agent and contacting the same with $H_3PO_4$, and which were calcined in dry air at 350° C. for six hours and subsequently calcined under a nitrogen/steam atmosphere at 415° C. for five hours at 20,000X magnification.

FIGS. 11 and 12 are scanning electron micrographs of phosphorus-vanadium mixed oxide catalyst particles, prepared under substantially anhydrous conditions by reduction of $V_2O_5$ in isobutyl alcohol in the presence of $H_3PO_4$ and in the absence of a corrosive reducing agent, and calcination in dry air at 400° C. for one hour, at 2,000X and 20,000X magnification, respectively. The catalysts appear to consist predominantly of clusters of small groups of associated platelets.

FIGS. 13–18 are scanning electron micrographs of phosphorus-vanadium mixed oxide catalyst precursor and catalyst particles of the instant invention. The precursors and catalysts of the instant invention exhibit a highly ordered and uniform spheroidal macrostructure. This structure appears to comprise generally spheroidal particles consisting of radially oriented three-dimensional networks of randomly shaped open cells, not unlike a honeycomb or an open cell sponge. Such a structure appears to be, and apparently is, ideal as a catalyst particle because of the apparent ease with which the reactant and product molecules can enter and exit the reactive surface.

The term "open cell", as employed herein refers to cells or void spaces in the catalyst precursor and catalyst materials which are interconnected in such a manner that gas can pass from one cell to another. This is as opposed to the term "close cell" wherein the cells or void spaces are discrete and the gas phase of such cell is independent of that of other cells.

Comparing the catalyst precursor and catalyst particles prepared in accordance with the instant process with those of the prior art indicates that those of the instant invention provide a greater number of potentially active and active catalytic sites per volume of catalyst precursor and catalyst, respectively, that are available to the hydrocarbon and molecular oxygen reactants during the preparation of maleic anhydride. This advantageously results in the catalysts of the instant process characteristically exhibiting a weight/weight productivity surprisingly greater than any phosphorus-vanadium mixed oxide catalyst heretofore known to the art, to wit, at least 70 g MAN/kg cat.-hr.

The catalysts of the instant process also possess a characteristically high intrinsic surface area which ranges from about 10 $m^2/g$ to about 40 $m^2/g$, even when consisting essentially of the mixed oxides of phosphorus and vanadium, that is, in the absence of promoter elements which, in general, would tend to cause an increase in intrinsic surface area of the mixed oxide due to their presence. It will be noted, however, that the inclusion of promoter element-containing compounds in the reaction mixture at a suitable point in order that the catalyst precursor, and ultimately the catalyst, contain the promoter elements if desired, is within the scope of the instant invention.

The surface area of the catalyst compositions of the instant process is measured using a Micromeritics Digisorb 2500 instrument according to the BET method [from Brunauer et al, *Journal of the American Chemical Society*, 60, 309–319 (1938)] described in ASTM D 3663-78. Krypton, however, is substituted for nitrogen as the adsorption gas for samples having a surface area of 10 $m^2/g$ or less for increased accuracy of measurement and reproducibility.

The catalysts of the instant process exhibit a phosphorus/vanadium atom ratio from about 0.5 to about 2.0, with a phosphorus/vanadium atom ratio of about 0.95 to 1.20 being preferred. In general, the phosphorus/vanadium atom ratio in the catalyst is determined by the phosphorus/vanadium atom ratio in the starting material as charged to the reactor. Since the catalyst precursor is normally recovered by filtration or centrifugation and decantation, the analyzed phosphorus/vanadium atom ratio is usually slightly less than the corresponding charged ratio. Typically, a phosphorus/vanadium (charged) atom ratio of 1.00 yields a catalyst having a phosphorus/vanadium (analyzed) atom ratio of 0.95 while a charged atom ratio of 1.20 yields a catalyst precursor (and catalyst) having an analyzed atom ratio of 1.00, thus indicating that a portion of the charged phosphorus is lost during the recovery step.

The catalysts prepared according to the process of the instant invention are useful in a variety of reactors to convert non-aromatic hydrocarbons to maleic anhydride. The catalysts may be used in a fixed-bed reactor using tablets, pellets, or the like, or in a fluid-bed reactor using catalysts preferably having a particle size of less than about 300 microns. Details of the operation of such reactors are well known to those skilled in the art.

The catalysts prepared in accordance with the instant process are particularly useful in fixed bed (tube), heat exchanger type reactors. The tubes of such reactors can vary in diameter from about 0.635 cm (0.25 inch) to about 3.81 cm (1.5 inches) and the length can vary from about 15.24 cm (6 inches) to about 304.8 cm (10 feet) or more. It is desirable to have the surfaces of the reactors at relatively constant temperatures, and some medium to conduct heat from the reactors is necessary to aid temperature control. Non-limiting examples of such media include Woods metal, molten sulfur, mercury, molten lead, and eutectic salt baths. A metal block reactor whereby the metal surrounding the tube acts as a temperature regulating body can also be used. The reactor or reactors can be constructed of iron, stainless steel, carbon steel, glass, and the like.

The reaction to convert non-aromatic hydrocarbons to maleic anhydride requires only contacting the hydrocarbons admixed with a molecular oxygen-containing gas (including molecular oxygen), such as air or molecular oxygen-enriched air, with the catalyst at elevated temperatures. In addition to the hydrocarbon and molecular oxygen, other gases, such as nitrogen or steam, may be present or added to the reactant feedstream. Typically, the hydrocarbon is admixed with the molecular oxygen-containing gas, preferably air, at a concentration of about one mole percent to about 10 mole percent hydrocarbon and contacted with the catalyst at a space velocity of about 100 $hr^{-1}$ to about 4,000 $hr^{-1}$ at a temperature between about 300° C. and about 600° C., preferably 1450 $hr^{-1}$ and about 325° C. to about 425° C., to provide an excellent yield of and selectively to maleic anhydride, and characteristically, a weight/weight productivity of at least 70 g MAN/kg cat.-hr at standardized conditions (as discussed hereinbelow).

The initial yield of maleic anhydride, however, may be low; and if this is the case, the catalyst, as will occur to those skilled in the art, can be "conditioned" by contacting the catalyst with low concentrations of hydrocarbon and molecular oxygen-containing gas at low space velocities for a period of time before production operations begin.

Pressure is not critical in the reaction to convert non-aromatic hydrocarbons to maleic anhydride. The reaction may be conducted at atmospheric, superatmospheric, or subatmospheric pressure. It will generally be preferred, however, for practical reasons to conduct the reaction at or near atmospheric pressure. Generally, pressures from about $1.013 \times 10^2$ kPa-G (14.7 psig, 1 atm) to about $1.38 \times 10^2$ kPa-G (20.0 psig) may be conveniently employed.

Maleic anhydride produced by using the catalysts prepared in accordance with of the instant process can be recovered by any means well known to those skilled in the art. For example, maleic anhydride can be recovered by direct condensation or by absorption in suitable media with subsequent separation and purification of the anhydride.

As previously noted, the catalysts of the instant process characteristically exhibit a weight/weight productivity of at least 70 g MAN/kg cat.-hr. The weight/weight productivity value is determined by carrying out the maleic anhydride (MAN) production under standardized conditions. Although any standardized set of conditions can be employed to establish a weight/weight productivity, the values reported herein are determined at a hydrocarbon-in-air concentration of 1.5 mole percent and 1450 $hr^{-1}$ space velocity while maintaining the hydrocarbon conversion within the range of 70 mole percent to 90 mole percent, preferably 78 mole percent to 80 mole percent. It will be recognized, of course, that while the weight/weight productivity as employed herein is determined at the previously stated standardized conditions, other conditions can be employed. However, weight/weight productivity values determined at conditions other than 1.5 mole percent hydrocarbon-in-air concentration and 1450 $hr^{-1}$ space velocity while maintaining the hydrocarbon conversion within the specified range, preferably 78 mole percent to 80 mole percent, generally will differ from those determined at the standardized conditions employed herein. As a result, direct comparison of weight/weight productivity values for different catalysts may be made only if such values are determined under the same standardized conditions.

A large number of non-aromatic hydrocarbons having from four to 10 carbon atoms can be converted to maleic anhydride using the catalysts prepared according to the instant process. It is only necessary that the hydrocarbon contain not less than four carbon atoms in a straight chain. As an example, the saturated hydrocarbon n-butane is satisfactory, but isobutane (2-methylpropane) is not satisfactory for conversion to maleic anhydride although its presence is not harmful. In addition to n-butane, other suitable saturated hydrocarbons include the pentanes, the hexanes, the heptanes, the octanes, the nonanes, the decanes, and mixtures of any of these, with or without n-butane so long as an unbranched chain having at least four carbon atoms is present in the saturated hydrocarbon molecule.

Unsaturated hydrocarbons are also suitable for conversion to maleic anhydride using the catalysts prepared according to the instant process. Suitable unsaturated hydrocarbons include the butenes (1-butene and 2-butene), 1,3-butadiene, the pentenes, the hexenes, the heptenes, the octenes, the nonenes, the decenes, and mixtures of any of these with or without the butenes, again, so long as the requisite unbranched $C_4$ hydrocarbon chain is present in the molecule.

Cyclic compounds such as cyclopentane and cyclopentene are also satisfactory feed materials for conversion to maleic anhydride.

Of the aforementioned feedstocks, n-butane is the preferred saturated hydrocarbon and the butenes are the preferred unsaturated hydrocarbons, with n-butane being most preferred of all feedstocks.

It will be noted that the aforementioned feedstocks need not necessarily be pure substances, but can be technical grade hyrocarbons.

The principal product from the oxidation of the aforementioned suitable feed materials is maleic anhydride, although small amounts of citraconic anhydride (methylmaleic anhydride) may also be produced when the feedstock is a hydrocarbon containing more than four carbon atoms.

The following specific examples illustrating the best currently-known method of practicing this invention are described in detail in order to facilitate a clear understanding of the invention. It should be understood, however, that the detailed expositions of the application of the invention while indicating preferred embodiments, are given by way of illustration only and are not be be construed as limiting the invention since various changes and modifications within the spirit of the invention will become apparent to those skilled in the art from this detailed description.

EXAMPLE 1

A twelve-liter, round bottom flask, fitted with a paddle stirrer, a thermometer, a heating mantle, an inlet gas dispersion frit, and a reflux condenser [attached to a Drierite ® (anhydrous calcium sulfate) drying tube and an off-gas water scrubber], was charged with 8000 ml of isobutyl alcohol, 117.6 g (0.41 mole) of zinc sulfate heptahydrate ($ZnSO_4.7H_2O$), and 744.3 g (4.10 moles) of vanadium pentoxide ($V_2O_5$). To this stirred mixture, 261.9 g (4.10 moles) of high purity sulfur dioxide ($SO_2$) was added over a two-hour period. Upon completion of the $SO_2$ addition, 906.5 g (9.82 moles) of phosphoric acid ($H_3PO_4$, 106.14% by weight) and 6.8 g (0.38 mole) of water were added to the mixture. The charged P/V atom ratio was about 1.20. The resulting mixture was then refluxed for 15 hours to give a bright blue mixture. The mixture was cooled to 40° C. and suction filtered to yield a blue solid. The blue solid was washed with fresh isobutyl alcohol and dried in an oven at 75° C. The P/V atom ratio of this precursor was 1.0. The average valence state for vanadium in the precursor was 4.0. The dry precursor was mixed with about one weight percent of powdered graphite (which served as a tableting lubricant) and pressed into 0.48-cm (0.1875-inch) diameter cylinders which had an average (side) crush strength of 4.45–8.90 newtons [N,1.00–2.00 pounds (lbs)]. The cylinders were then dried in air in a forced-draft oven for nine hours at 150° C., followed by heat treatment at 350° C. for six hours to yield an oxidized catalyst precursor having an average vanadium valence of 4.4. The oxidized precursor tablets were placed in a tube furnace and heated from room temperature to about 280° C. under a nitrogen purge. When the temperature reached 280° C., the nitrogen purge stream was mixed with molecular oxygen-free steam to provide a 34 volume percent water (steam)/66 volume percent nitrogen gas mixture. This nitrogen/steam mixture was passed over the catalyst at about 1240 $hr^{-1}$ total space velocity and heating continued to about 415° C. This temperature and nitrogen/steam gas flow were maintained over the catalyst for about five hours. At the end of this five-hour period, the catalyst was cooled to room temperature and characterized. The catalyst was performance tested by charging a portion of the catalyst to a 2.54-cm (1-inch) inside diameter×121.92-cm (4-foot) long tubular fixed-bed reactor purged with dry nitrogen. When the temperature of the reactor reached 375° C., the nitrogen flow was terminated and a feed stream containing 1.5 mole percent n-butane-in-air at a space velocity of 1450 $hr^{-1}$ was passed over the catalyst. The properties of the catalyst and the performance results, respectively, are tabulated in Table 1 and Table 2.

EXAMPLE 2

A five-liter, round-bottom flask equipped as described in Example 1 (except for the inlet gas frit) was charged with 3000 ml of isobutyl alcohol, 44.7 g (0.16 mole) of $ZnSO_4.7H_2O$, 20 ml of fuming sulfuric acid (30% $SO_3$), 282.8 g (1.55 mole) of $V_2O_5$, and 350.0 g (3.79 moles) of $H_3PO_4$ (106.14% by weight). The charged P/V atom ratio was about 1.22. The resulting mixture was refluxed, with stirring, for five hours to give a bright blue mixture. The blue mixture was cooled to about 40° C. and suction filtered. The blue solid was thoroughly washed with fresh isobutyl alcohol and dried in an oven at 75° C. The P/V atom ratio of the precursor was 1.00 and its average vanadium valence was 4.0. The dry precursor was mixed with about one weight percent of powdered graphite and pressed into a 0.48-cm (0.1875-inch) diameter cylinder which had an average (side) crush strength of 4.45–8.90N (1.00–2.00 lbs). The precursor tablets were dried in air in a forced draft oven at 225° C. for two hours, then air calcined at 350° C. for six hours to give an oxidized precursor with an average valence of 4.5. The oxidized precursors were then calcined under a nitrogen/steam atmosphere, characterized, and performance tested all as described in Example 1. The parameters and results are tabulated in Tables 1 and 2.

EXAMPLE 3

A three-liter, round bottom flask, equipped as described in Example 1, was charged with 1000 ml of isobutyl alcohol and 100.0 g (0.55 mole) of $V_2O_5$ to give a mixture to which was added 422.0 g (3.30 moles) of anhydrous hydrogen iodide (HI) and 109.3 g of $H_3PO_4$ (100.54%) of containing 100 ml of isobutyl alcohol. The charged P/V atom ratio was about 1.025. The resulting solution was refluxed for three hours, then distilled until 650 ml of distillate had been removed. An additional 250 ml of isobutyl alcohol was added to the still pot residue and the resulting mixture was again distilled, this time until 250 ml of distillate had been collected. The remaining blue-green slurry was cooled to 60° C. and suction filtered to give a blue solid. The blue solid was washed with 500 ml of isobutyl alcohol, followed by 1000 ml of acetone, and then air dried at room temperature for about 60 hours. The resulting bright blue catalyst precursor had a P/V atom ratio of 0.95 and an average vanadium valence of 4.0. The precursor was mixed with one weight percent of powdered graphite and pressed into 0.48-cm (0.1875-inch) diameter cylinders having an average (side) crush strength of 13.34N (3.00 lbs). The precursor tablets were then calcined in air at 400° C. for six hours to give a catalyst having an average vanadium valence of 4.5. The resulting catalyst tablets were charged to a tubular fixed-bed reactor like that described in Example 1 and performance tested at 1450 $hr^{-1}$, 1.5 mole percent n-butane-in-air concentration. The parameters and results are tabulated in Tables 1 and 2.

EXAMPLE 4

Catalyst precursor powder was prepared as described in Example 1 except that $ZnSO_4.7H_2O$ was omitted as a component of the reaction mixture. The catalyst precursor had a P/V atom ratio of 1.01 and an average vanadium valence of 4.0. The precursor was mixed with one weight percent of powdered graphite and pressed into 0.48-cm (0.1875-inch) diameter cylinders having an average (side) crush strength of 13.34N (3.00 lbs). The cylinders were heated in air at 225° C. for about 14 hours, then calcined at 400° C. for six hours to give an oxidized catalyst with an average vanadium valence of 4.55. The catalyst tablets were characterized and performance testing as described in Example 1. The parameters and results are tabulated in Tables 1 and 2.

EXAMPLE 5

Isobutyl alcohol (8960 ml) and 833.4 g (4.58 moles) of $V_2O_5$ were charged to the reactor described in Example 1. To this stirred mixture was added 293.4 g (4.58 moles) of $SO_2$ over a 2.5-hour period. To the resulting mixture were added 843.1 (9.16 moles) of $H_3PO_4$ (106.5%) and 54.9 (3.05 moles) of water. The charged P/V atom ratio was 1.00. The mixture was then refluxed over 20 hours to give a bright blue suspension. The mixture was cooled to room temperature and suction filtered to give a bright blue filter cake of catalyst precursor. The precursor was washed with acetone and dried in air at room temperature. The precursor had a P/V atom ratio of 0.95 and an average vanadium valence of 4.0. The precursor was mixed with one weight percent of powdered graphite and pressed into 0.48-cm (0.1875-inch) diameter cylinders having an average (side) crush strength of 13.34N (3.00 lbs). The tablets were then heat treated in air at 250° C. in a forced draft oven for 15 hours. The tablets were charged to a tubular fixed-bed reactor and heated under an air purge to 275° C. When the temperature reached 275° C., n-butane (1.5 mole percent) was added to the air stream to give a total space velocity of 1450 $hr^{-1}$. Heating was continued to 350° C. and the reactor temperature was adjusted to ensure that the maximum temperature in the catalyst bed did not exceed 400° C. for the first 100 hours on test. For the next 100 hours on test, the bath temperature was adjusted such that the maximum temperature did not exceed 415° C. The parameters and results are tabulated in Tables 1 and 2.

EXAMPLE 6

Catalyst precursor powder was prepared as described in Example 1. The dry precursor powder was mixed with one weight percent of powdered graphite and pressed into 0.56-cm (0.22-inch) diameter cylinders. The cylinders were dried at 150° C. for about 15 hours, calcined in dry air at 350° C. for six hours, then treated with a 64/36 volume percent nitrogen/steam gaseous mixture at 500° C. and 276 $hr^{-1}$ space velocity. These tablets, after cooling to room temperature, were charged to a tubular fixed-bed reactor like that described in Example 1 and performance tested at 1450 $hr^{-1}$ and 1.5 mole percent n-butane-in-air concentration. The parameters and results are tabulated in Tables 1 and 2.

EXAMPLE 7

This Example illustrates the use of an organic surfactant as the alcohol-modifying agent.

Isobutyl alcohol (750 ml), 112.5 g (0.62 mole) of $V_2O_5$, 137.1 g (1.48 moles) of $H_3PO_4$ (106.14%, P/V atom ratio of 1.20), and 2.4 g of surfactant material [prepared by reacting 100.0 g of $H_3PO_4$ (115%), 100.0 g of 65% oleum (fuming sulfuric acid), and 210.0 g of mixed alkylbenzenes] were charged to a three-liter, round bottom flask equipped as described in Example 1 (except for the inlet gas frit). The mixture was heated to reflux and maintained at reflux for six hours to give a blue mixture. The blue mixture was cooled to room temperature and suction filtered to yield a blue filter cake. The blue filter cake was washed with fresh isobutyl alcohol and dried in an oven at 75° C. The P/V atom ratio of the dry precursor powder was 0.99 and the average vanadium valence was 4.0. The dry precursor powder was mixed with one weight percent of powdered graphite and pressed into 0.48-cm (0.1875-inch) cylinders which had an average (side) crush strength of 8.90N (2.00 lbs). The cylinders (tablets) were then heated in air at 150° C. for about 15 hours, followed by heat treatment (calcination) at 350° C. for six hours to give an oxidized precursor with an average vanadium valence of 4.4. The heat-treated tablets were then calcined under a nitrogen/-steam atmosphere at 400° C., cooled to room temperature, and charged to a tubular fixed-bed reactor purged with nitrogen and performance tested all as described in Example 1. The parameters and results are tabulated in Tables 1 and 2.

EXAMPLE 8 (Comparative)

This Example illustrates the effect of temperature and prolonged heating of the catalyst precursor on catalyst performance.

The catalyst precursor and tablets therefrom were prepared as described in Example 5. The tablets were subjected to an extended heat treatment at 275° C. (163 hours). The resultant tablets were nitrogen/-steam calcined at 64 volume percent nitrogen/36 volume percent steam and 400° C. for about 8.5 hours. The catalyst was cooled to room temperature and performance tested in a 2.54-cm (1-inch) inside diameter×121.92-cm (4-foot) long tubular fixed-bed reactor at 1450 $hr^{-1}$ space velocity and 1.5 mole percent n-butane-in-air concentration. The parameters and results are tabulated in Tables 1 and 2.

EXAMPLE 9 (Comparative)

This Example illustrates the effect of high density structures (tablets) on the performance of the catalyst.

A twelve liter, round bottom flask equipped as described in Example 1 was charged with 7000 ml of isobutyl alcohol and 744.13 g (4.10 moles) of high purity $V_2O_5$. To this agitated slurry was added 262.0 g (4.10 moles) of high purity $SO_2$ gas over a one-hour period. During the $SO_2$ addition, the temperature of the mixture rose from 22° C. to 32° C. The mixture was heated to reflux and maintained at this temperature overnight (approximately 16 hours). The resulting orange-green mixture was cooled to 40° C. and 906.53 g (9.82 moles) of $H_3PO_4$ (106.14%, P/V atom ratio of 1.20) and 58.4 g (3.24 moles) of water were added along with one liter of isobutyl alcohol. The mixture was refluxed overnight (approximately 16 hours) to yield a blue mixture which was cooled to 45° C. and suction filtered. The filter cake was washed with acetone and air dried at room temperature (P/V atom ratio of 1.02). A portion (100.0 g) of the dry powder was blended with 1.0 g of powdered graphite and formed into 0.48 cm diameter×0.40 cm long tablets (0.1875 inch×0.157 inch) having an average (side) crush strength of 62.28N (14.00 lbs). The tablets were heat treated in air at 260° C. for 24 hours, thereby causing an increase in the average crush strength to 222.41 (50 lbs). The heat treated tablets were then calcined in dry air at 350° C. for eight hours, followed by a 77.2 volume percent nitrogen/22.8 volume percent steam calcination at 400° C. for five hours in a vertical 2.54-cm (1-inch) inside diameter calciner tube.

The catalyst was performance tested as described in Example 8. The parameters and results are tabulated in Tables 1 and 2.

EXAMPLE 10 (Comparative)

This Example, prepared according to the procedure described in Example 4 of U.S. Pat. No. 3,864,280, illustrates a typical prior art catalyst prepared in a substantially anhydrous organic medium.

A three-liter, round-bottom flask fitted with a paddle stirrer, thermometer, gas inlet frit, reflux condenser, water scrubber, and heating mantle was charged with one liter of isobutyl alcohol and 181.88 g (1.00 mole) of $V_2O_5$. The mixture was kept suspended by moderate stirring at 24° C. Dry HCl gas was slowly added to the stirred mixture such that the reaction temperature did not exceed 40° C. During the HCl addition period, the solids in the flask gradually dissolved. When all of the solids were dissolved, resulting in a dark red-brown solution, addition of HCl gas was stopped. A second flask containing 200.0 g (2.041 moles) of 100% $H_3PO_4$ in 100 ml of isobutyl alcohol was substituted for the initial flask containing the vanadium/HCl/isobutyl alcohol solution. Contents of the initial flask were slowly added to the second flask with stirring. The vanadium solution was quantitatively transferred to the $H_3PO_4$ solution by rinsing with an additional 100 ml of isobutyl alcohol. This final solution was heated to reflux with stirring (107°–108° C.) and allowed to reflux for 1.5 hours. During this time the solution turned dark blue and a small quantity of blue crystals formed in the flask. After the reflux period, a distillation condenser was substituted for the reflux condenser and distillation started. A total of 780 ml of distillate was collected, at which time the mixture was a thick blue slurry. This slurry was cooled to 80° C. and quantitatively transferred to a porcelain dish and dried for 48 hours at 150° C.

The dry grey-blue cake was ground to pass a 60 mesh screen (U.S. Standard Sieve Size). This powder was dry blended with one weight percent of powdered graphite and formed into 0.48 cm × 0.48 cm (0.1875 inch × 0.1875 inch) cylinders on a tableting machine. A 105.0 g sample of the tablet was then calcined. A dry air purge (9 liters/minute) was passed over the catalyst, beginning at three hours into the heat up/hold period. At the end of the six hour period at 400° C., the tablets were cooled to room temperature to yield 91.1 g of calcined catalyst. A portion (42.0 g) of the catalyst was charged to a 2.54-cm (1-inch) inside diameter × 15.24-cm (6-inch) long fixed-bed tubular reactor and performance tested. The results and parameters are tabulated in Tables 1 and 2.

EXAMPLE 11 (Comparative)

This Example illustrates a typical prior art catalyst prepared in an aqueous medium using a trivalent phosphorus compound (phosphorous acid) as the reducing agent. The catalyst was prepared according to Example I of U.S. Pat. No. 3,907,707 using 133.08 g (0.73 mole) of $V_2O_5$, 450 ml of water, 50.6 g (0.44 mole) of 85% phosphoric acid, and 91.7 g (1.11 moles) of 99.4% phosphorus acid (P/V atom ratio of 1.06) except that the phosphorus-vanadium mixed oxide precursor, after collection by filtration and washing, was dried in an oven at 130° C. Dry material was blended with one weight percent of powdered graphite and formed into 0.48-cm (0.1875-inch) cylinders and calcined in dry air at 400° C. for six hours. The resulting catalyst was charged to a tubular, fixed-bed reactor and performance tested as described in Example 8. The parameters and results are tabulated in Tables 1 and 2.

EXAMPLE 12 (Comparative)

Catalyst precursor powder was prepared as described in Example 12. The dry granulated powder was formed into about 0.50 cm diameter spheroids by feeding the powder onto a 40.64 cm (16 inch) inside diameter disc of a disc pelletizer at a constant rate while selectively wetting the powder with between about 30% and 35% by weight water, based on the dry weight of the catalyst precursor. The moist spheroids were collected, air dried, and then heated to 120° C. to evaporate any remaining traces of water. The dry spheroids were heat treated at 250° C. for about four hours and then calcined in dry air at 400° C. for six hours. The calcined spheroids were charged to a 2.54-cm (1-inch) inside diameter × 15.24-cm (6-inch) long tubular, fixed-bed reactor and performance tested under conditions described in Example 8. The parameters and results are tabulated in Tables 1 and 2.

EXAMPLE 13

This Example illustrates an early prior art catalyst prepared in an aqueous medium using hydrochloric acid as the reducing agent. The catalyst was prepared according to the procedure described in Example 2 of U.S. Pat. No. 3,293,268.

A three-liter, round bottom flask fitted with a paddle stirrer, thermometer, addition funnel, reflux condenser, water scrubber, and heating mantle was charged with 1750 ml of 12N hydrochloric acid (HCl) and 134.4 g (0.74 mole) of $V_2O_5$. The mixture was stirred at a moderate rate to maintain the solids in suspension and heated to 90° C. over a two-hour period to give a blue solution. To this solution was added, over a 20-minute period, 177.6 g (1.55 moles) of 85.7% phosphoric acid (P/V atom ratio of 1.05). During the phosphoric acid addition, the reaction temperature did not exceed 91° C. The reaction mixture was cooled to 70° C. and transferred to a porcelain dish and dried in an oven at 130° C. for about 50 hours. The dry material was then heated in air at 365° C. for two hours. The resulting heat treated material was granulated and blended with two weight percent of powdered graphite and formed into 0.48 cm × 0.48 cm (0.1875 inch × 0.1875 inch) cylinders on a tableting machine. The tablets were calcined in dry air for six hours at 400° C. The catalyst was performance tested as described in Example 8. The parameters and results are tabulated in Tables 1 and 2.

EXAMPLE 14 (Comparative)

This Example illustrates a typical prior art catalyst prepared in a substantially anhydrous organic medium and containing zinc and lithium as added promoter elements. The catalyst was prepared according to the procedure described for Example 21 in U.S. Pat. No. 4,251,390.

A three-liter, round bottom flask equipped with an overhead stirrer, gas inlet tube, thermometer, and Dean Stark trap with water condenser was charged with 1703 ml of anhydrous isobutyl alcohol and 300.0 g (1.65 moles) of $V_2O_5$. Approximately 1496.0 g (41.0 moles) of dry HCl gas was passed into the stirred suspension at a rate sufficient to maintain the reaction temperature at or below 50° C. To the resulting solution was added a solution consisting of 300 ml of isobutyl alcohol, 280.95 g (2.45 moles) of 85.5% $H_3PO_4$, and 106.99 g (0.75 mole) of $P_2O_5$. An additional 96 ml of isobutyl alcohol was used to rinse the phosphorus-containing solution into the vanadium-containing solution. Anhydrous $ZnCl_2$ (4.5 g, 0.033 mole) and 0.28 g (0.0066 mole) of LiCl were then added to the reaction mixture. The mixture was heated and distilled to give about 1800 ml of distillate. The resulting slurry was dried overnight (approximately 16 hours) at 150° C. and then heat treated at 260° C. for three hours. The dry material was blended with one weight percent of powdered graphite and formed into 0.48 cm (0.1875 inch) cylinders on a Stokes tableting machine. The tablets were charged to a 2.54-cm (1-inch) inside diameter by 121.92-cm (4-foot) long tubular fixed-bed reactor and conditioned by a slow heat up of the catalyst to operating temperature at a rate of 5° C. to 10° C. per hour while adjusting the gas flow from 0.5 to 1.0 mole percent n-butane-in-air at an initial space velocity (Gaseous Hourly Space Velocity, GHSV) of 900 $hr^{-1}$ up to 2500 $hr^{-1}$ to maintain the desired conversion level. The catalyst was performance tested at 1450 $hr^{-1}$ space velocity and 1.5 mole percent n-butane-in-air as described in Example 8. The parameters and results are tabulated in Tables 1 and 2.

EXAMPLE 15 (Comparative)

This Example illustrates a typical prior art catalyst prepared in a substantially anhydrous organic medium in the absence of a corrosive reducing agent. The catalyst was prepared according to the procedure described in Example 1 of U.S. Pat. No. 4,333,853.

A three-liter, round bottom flask equipped as described in Example 2 was charged with 1300 ml of isobutyl alcohol 90.95 g (0.50 mole) of $V_2O_5$, and 117.6 g (1.20 moles) of $H_3PO_4$ (100%). The charged P/V atom ratio was 1.20. The mixture was heated to reflux and maintained at reflux for about 16 hours with constant agitation. The resulting blue slurry was cooled and suction filtered to give a blue product which was dried at ambient temperature under vacuum, and then dried for about 2.5 hours in air at 145° C. The P/V atom ratio of the precursor was 1.00 (in contrast to the P/V atom ratio of 1.20 claimed by the patent) and its average vanadium valence was 4.0. The precursor was mixed with one weight percent of powdered graphite and pressed into 0.48-cm (0.1875-inch) cylinders. The cylinders (tablets) were calcined in dry air at 400° C. for one hour. The calcined catalyst was performance tested as described in Example 8. The parameter and results are tabulated in Tables 1 and 2.

EXAMPLE 16 (Comparative)

In order to obtain a catalyst prepared in accordance with the procedure described in Example 1 of U.S. Pat. No. 4,333,853 and having a P/V atom ratio of 1.20, the catalyst precursor slurry was reduced to dryness rather than filtered as in Example 15.

A twelve-liter, round bottom flask equipped as described in Example 2 was charged with 10,000 ml of isobutyl alcohol, 606.3 g (3.33 moles) of $V_2O_5$, and 784.8 g (8.00 moles) of 100% $H_3PO_4$. The charged P/V atom ratio was 1.20. The mixture was heated to reflux and maintained at reflux for 18 hour. The resulting blue slurry was partially distilled to give a viscous blue slurry. The slurry was placed in porcelain dishes and dried under vacuum at 150° L C. for three hours to yield a catalyst precursor having a P/V atom ratio of 1.20. The dry precursor was formed into 0.48-cm tablets and calcined as described in Example 16. The calcined catalyst was performance tested as described in Example 8. The parameters and results are tabulated in Tables 1 and 2.

EXAMPLE 17

To a five liter, round bottom flask, fitted as in previous experiments, was added 3733 ml of isobutyl alcohol, 347.23 g (1.91 moles) of $V_2O_5$, and 122.23 g (1.91 moles) of $SO_2$ gas. The mixture was refluxed for 24 hours, after which time very little reduction had occurred. To the hot solution was added 421.5 g (4.58 moles) of $H_3PO_4$ (106.51%) and 27.4 g (1.52 moles) of water (P/V atom ratio of 1.20). Reflux was continued for five additional hours to yield a blue mixture which was cooled to 50° C. and suction filtered. The filtrate was very pale green, indicating a small amount of soluble vanadium species. The filter cake was washed with isobutyl alcohol, then acetone, and then air dried at room temperature overnight to give the dry catalyst precursor powder which was found to have a P/V atom ratio of 1.01.

This dry powder was mixed with one weight percent of powdered graphite and formed into 0.48 cm×0.48 cm (0.1875 inch×0.1875 inch) having an average (side) crush strength of 8.90N (2 lbs). The precursor tablets were dried at 250° C. for 15 hours, then air calcined at 2(400)6 in air. The air calcined catalyst was nitrogen/steam calcined in a vertical 2.54-cm (1-inch) inside diameter tube at about 330° C. for about eight hours with a 38 volume percent nitrogen/62 volume percent water flow over the catalyst at about 2750 $hr^{-1}$ space velocity. The catalyst was cooled to room temperature and performance tested as described in Example 8. The parameters and results are tabulated in Tables 1 and 2.

EXAMPLE 18

A three-liter round bottom flask equipped as described in Example 1 was charged with 1000 ml of isobutyl alcohol, 29.41 g (0.10 mole) of $ZnSO_4.7H_2O$, 186.03 g (1.022 moles) of high purity $V_2O_5$ and additional 1000 ml of isobutyl alcohol. To this agitated slurry was added, over a 25 minute period, 65.5 g (1.023 moles) of high purity $SO_2$ gas through the gas-dispersion tube well immersed in the slurry mixture. During the $SO_2$ addition, the temperature of the reaction rose from 22° C. to 38° C. Upon completion of the $SO_2$ addition, 1.7 g (0.094 mole) of deionized water and 226.63 g (2.45 moles) of $H_3PO_4$ (106.14% P/V atom ratio of 1.20) were added to the mixture. The mixture was heated to reflux and maintained at reflux for two hours and 45 minutes. The resulting blue mixture was cooled to 45° C. and suction filtered. The filter cake was suspended in fresh isobutyl alcohol, agitated for one hour, and suction filtered. The filter cake was placed in a shallow pan and dried over a weekend (approximately 64 hours) at room temperature to yield a mildly agglomerated powder which was passed through a 60 mesh (U.S. Standard Sieve Size) screen. A portion (100.0 g) of the powder was mixed with 1.0 g of powdered graphite and formed into 0.48-cm (0.1875-inch) tablets. The tablets, having an average (side) crush strength of about 4.45N (1.00 lb), were tray dried at 150° C. in a forced draft oven for 60 hours, followed by calcination under a 9–10 liters/-minute air purge at 350° C. for six hours. The air calcined tablets (average vanadium valence of 4.4) were then subjected to a 64 volume percent nitrogen/36 volume percent steam calcination at 400° C.±5° C. and 335 $hr^{-1}$ gaseous space velocity for five hours. The catalyst was performance tested as described in Example 8 using several space velocities and different feed concentration to show the effect on weight/weight productivity values. The parameters and results are tabulated in Tables 1 and 2.

EXAMPLE 19

The remaining catalyst precursor powder from Example 18 was mixed with one weight percent of powdered graphite and formed into 0.56 cm (0.22 inch) tablets. The tablets, having an average (side) crush strength of 4.45N (1.00 lb), were dried in a forced-draft oven at 150° C. for approximately 15 hours. The dried tablets were air calcined at 350° C. for six hours with a 9–10 liters/minute air purge (average vanadium valence of about 4.04). A portion (38.25 g, 85 ml) of the air calcined tablets were then calcined under a 64 volume percent nitrogen/36 volume percent steam atmosphere at 500° C. and 276 hr$^{-1}$ space velocity for four hours in a 2.54-cm inside diameter calcination tube. The resulting catalyst was performance tested as described in Example 8. The parameters and results are tabulated in Tables 1 and 2.

EXAMPLE 20

A portion (38.2 g, 85 ml) of the air calcined tablets from Example 19 was calcined under a nitrogen/steam atmosphere as described in Example 19 except that the calcination period was five hours. The catalyst was then performance tested as described in Example 8. The parameters and results are tabulated in Tables 1 and 2.

EXAMPLE 21

A portion (39.1 g, 85 ml) of the air calcined tablets from Example 19 was calcined under a nitrogen/steam atmosphere as described in Example 19 except that the temperature was 406° C., the gaseous space velocity was 441 hr$^{-1}$, and the calcination period was three hours.

EXAMPLE 22

This Example illustrates the preparation of a lithium-zinc promoted catalyst.

A twelve-liter, round bottom flask equipped as described in Example 1 was charged with 7466 ml of isobutyl alcohol and 694.46 g (3.82 moles) of high-purity $V_2O_5$. To this mixture was added 244.5 g (3.82 moles) of high-purity $SO_2$ gas at the rate of about 2 g/-minutes. Thereafter, 10.41 g (0.0763 mole) of anhydrous zinc chloride ($ZnCl_2$, Zn/V atom ratio of 0.010) and 0.65 g (0.015 mole) of lithium chloride (LiCl, Li/V atom ratio of 0.0020) were added as solids. The resulting mixture was refluxed for 24 hours, during which time the color of the mixture changed from orange to a dirty brown with a greenish tint. While the mixture was at reflux, 846.01 g (9.16 moles) of $H_3PO_4$ (106.14%, P/V atom ratio of 1.20) and 54.5 g (3.028 moles) of water were added, causing a vigorous reaction. Reflux was continued for 9.5 hours, resulting in a blue mixture. Upon completion of the reflux, the blue mixture was cooled to room temperature and suction filtered. The blue filter cake was washed with 1.69 liters (0.5 gallon) of acetone and air dried at room temperature for approximately 60 hours to give a blue powder having a P/V atom ratio of 1.01 and a Zn/V atom ratio of 0.0095. The dry powder was mixed with one weight percent of powdered graphite and formed into 0.48 cm × 0.48 cm (0.1875 inch × 0.1875 inch) tablets. The tablets were heat treated in air at 250° C. for 15 hours and calcined in flowing air at 0.5(350)6, (heat from room temperature to 350° C. over 0.5 hour and maintain the 350° C. for six hours). The air calcined tablets were nitrogen/steam calcined in a vertical 3.0 cm inside diameter tube at 400°· C. for about five hours with 64 volume percent nitrogen/36 volume percent water flow over the catalyst at about hr$^{-1}$ space velocity. The catalyst was cooled to room temperature. Performance testing was not carried out on this catalyst at 1450 hr$^{-1}$. The parameters and results are tabulated in Tables 1 and 2.

TABLE 1

| | | | | CATALYST | | | | | |
|---|---|---|---|---|---|---|---|---|---|
| EX. | NO. | EMPIRICAL FORMULA[1] | FORM (SIZE, cm) | P/V ATOM RATIO | AVERAGE VANADIUM VALENCE | POROSITY % | MEAN PORE DIAMETER $\mu m$ | TOTOAL PORE VOLUME cc/g | BET SURFACE AREA $m^2/g$ |
| 1 | 1 | $P_{1.0}V_{1.0}Zn_{0.05}O_x$ | Tablets (0.48) | 1.00 | 4.40 | 60.30 | 0.12 | 0.80 | 25.00 |
| 2 | 2 | $P_{1.0}V_{1.0}Zn_{0.05}O_x$ | " | 1.00 | 4.50 | 58.60 | 0.11 | 0.76 | 19.00 |
| 3 | 3 | $P_{0.95}V_{1.0}O_x$ | " | 0.95 | 4.48 | 62.10 | 0.15 | 0.83 | 18.00 |
| 4 | 4 | $P_{1.01}V_{1.0}O_x$ | " | 1.01 | 4.55 | —[3] | —[3] | —[3] | 20.00 |
| 5 | 5 | $P_{0.95}V_{1.0}O_x$ | " | 0.95 | 4.05 | —[3] | —[3] | —[3] | 16.00 |
| 6 | 6 | $P_{1.0}V_{1.0}Zn_{0.95}O_x$ | Tablets (0.56) | 1.00 | 4.52 | 68.20 | 0.16 | 0.85 | 22.00 |
| 7 | 7 | $P_{0.99}V_{1.0}O_x$ | Tablets (0.48) | 0.99 | 4.40 | 60.50 | 0.12 | 0.79 | —[3] |
| 8[2] | 8 | $P_{0.95}V_{1.0}O_x$ | " | 0.95 | 4.46 | 55.85 | 0.15 | 0.35 | —[3] |
| 9[2] | 9 | $P_{1.02}V_{1.0}O_x$ | " | 1.02 | 4.60 | 18.00 | 0.03 | 0.09 | —[3] |
| 10[2] | 10 | $P_{0.98}V_{1.0}O_x$ | " | 0.98 | 4.50 | 35.50 | 0.16 | 0.23 | 9.30 |
| 11[2] | 11 | $P_{1.06}V_{1.0}O_x$ | " | 1.06 | 4.80 | 32.00 | 0.10 | 0.30 | 5.60 |
| 12[2] | 12 | $P_{1.06}V_{1.0}O_x$ | Spheroids (0.50) | 1.06 | 4.16 | 61.20 | 0.25 | 0.47 | 7.40 |
| 13[2] | 13 | $P_{1.05}V_{1.0}O_x$ | Tablets (0.48) | 1.05 | 4.72 | 31.30 | 0.12 | 0.18 | 4.20 |
| 14[2] | 14 | $P_{1.2}V_{1.0}Zn_{0.01}Li_{0.002}O_x$ | Tablets (0.48) | 1.20 | 3.86 | 29.20 | 0.15 | 0.17 | —[3] |
| 15[2] | 15 | $P_{1.0}V_{1.0}O_x$ | " | 1.00 | 4.32 | —[3] | —[3] | —[3] | —[3] |
| 16[2] | 16 | $P_{1.20}V_{1.0}O_x$ | " | 1.20 | 4.18 | —[3] | —[3] | —[3] | —[3] |
| 17 | 17 | $P_{1.01}V_1O_x$ | " | 1.01 | 4.60 | 61.98 | 0.11 | 0.48 | —[3] |
| 18 | 18 | $P_{1.01}V_{1.0}Zn_{0.05}O_x$ | " | 1.01 | 4.36 | 65.10 | 0.11 | 0.62 | 17.00 |
| 19 | 19 | $P_{1.11}V_{1.0}O_x$ | Tablets (0.56) | 1.11 | 4.04 | 72.54 | 0.15 | 0.90 | 21.00 |
| 20 | 20 | $P_{1.01}V_{1.0}Zn_{0.05}O_x$ | " | 1.01 | 4.03 | 68.89 | 0.12 | 0.83 | —[3] |
| 21 | 21 | $P_{1.01}V_{1.0}Zn_{0.05}O_x$ | " | 1.01 | 4.02 | 69.25 | 0.11 | 0.82 | —[3] |
| 22 | 22 | $P_{1.0}V_{1.0}Zn_{0.0095}Li^3$ | " | 1.00 | 4.56 | 56.24 | 0.090 | 0.36 | —[3] |

[1]Subscript x is a number taken to satisfy the valence requirements of the other elements present.
[2]Comparative example.
[3]Not determined.

TABLE 2[1]

| CAT. No. | CATALYST REACTOR CHARGE DENSITY (kg/m³) × 10³ | BATH TEMPERATURE °C. | CONV. mole % | SEL. mole % | YIELD mole % | PRODUCTIVITY WT/VOL. (g MAN/-m³ cat.-hr) × 10⁴ | WT/WT g MAN/-kg cat.-hr. |
|---|---|---|---|---|---|---|---|
| 1 | 0.52 | 360 | 82.0 | 73.8 | 60.5 | 4.99 | 96.0 |
| 2 | 0.56 | 346 | 87.0 | 70.0 | 60.0 | 5.38 | 96.0 |
| 3 | 0.52 | 361 | 80.0 | 66.2 | 53.0 | 4.78 | 92.0 |
| 4 | 0.52 | 360 | 80.0 | 66.2 | 53.0 | 4.84 | 93.0 |
| 5 | 0.60 | 364 | 72.0 | 68.0 | 49.0 | 4.44 | 74.0 |
| 6 | 0.40 | 380 | 80.0 | 65.0 | 52.0 | 4.68 | 117.0 |
| 7 | 0.60 | 376 | 80.0 | 68.0 | 54.4 | 4.87 | 81.2 |
| 8[2] | 0.83 | 382 | 79.5 | 65.1 | 51.7 | 4.79 | 57.7 |
| 9[2] | 1.19 | 427 | 79.5 | 52.0 | 41.3 | 3.84 | 32.3 |
| 10[2] | 0.84 | 406 | 79.3 | 66.0 | 52.4 | 4.81 | 57.3 |
| 11[2] | 1.03 | 413 | 80.0 | 66.2 | 53.0 | 4.82 | 46.9 |
| 12[2] | 0.75 | 418 | 80.0 | 68.8 | 55.0 | 4.97 | 66.3 |
| 13[2] | 0.92 | 407 | 79.0 | 62.1 | 49.1 | 4.32 | 47.0 |
| 14[2] | 1.02 | 396 | 80.0 | 65.0 | 52.0 | 5.56 | 54.5 |
| 15[2] | 0.73 | 400 | 80.0 | 62.5 | 50.0 | 2.80 | 61.5 |
| 16[2] | 0.73 | 398 | 79.0 | 63.3 | 50.0 | 2.81 | 61.6 |
| 17 | 0.62 | 376 | 79.0 | 69.9 | 55.2 | 4.95 | 79.8 |
| 18 | 0.54 | 372 | 79.1 | 72.6 | 57.4 | 5.13 | 95.0 |
| 18[3,4] | " | 379 | 71.0 | 65.7 | 46.7 | 7.56 | 140.0[3,4] |
| 18[3,5] | " | 364 | 79.0 | 71.6 | 56.6 | 4.067 | 75.3[3,5] |
| 18[3,6] | 0.54 | 363 | 80.0 | 66.8 | 53.4 | 5.062 | 47.7[3,6] |
| 19 | 0.40 | 385 | 80.4 | 64.5 | 51.8 | 4.60 | 115.0 |
| 20 | 0.40 | 385 | 80.7 | 59.1 | 47.7 | 4.26 | 106.5 |
| 21 | 0.40 | 374 | 79.3 | 64.4 | 51.0 | 4.60 | 115.0 |
| 22[4] | 0.69 | 394 | 71.4 | 62.3 | 44.5 | 4.54 | 105.4[4] |

[1]All performance tests were conducted at a concentration of 1.5 mole percent n-butane in air and a space velocity of 1450 hr⁻¹ under a pressure of 1.055 × 10² kPa-G (15.3 psig) unless otherwise indicated.
[2]Comparative catalyst.
[3]Comparison performance tests were run to illustrate the variation in the weight/weight productivity values at different feed stream space velocities and different concentrations of n-butane in-air.
[4]The performance test was conducted at a space velocity of 2600 hr⁻¹ instead of the standard 1450 hr⁻¹, thereby giving a higher weight/weight productivity value. This increase effectively prevents a direct comparison between weight/weight productivity values determined under different conditions (in this case, at a different space velocity).
[5]The performance test was conducted at a space velocity of 1150 hr⁻¹ instead of the standard 1450 hr⁻¹, thereby giving a lower weight/weight productivity value. This decrease effectively presents a direct comparison between weight/weight productivities values determined under different conditions (in this case, at a different space velocity).
[6]The performance test was conducted at a concentration of 2.0 mole percent n-butane in air and a space velocity of 1150 hr⁻¹ instead of the standard concentration of 1.5 mole percent n-butane-in-air and a space velocity of 1450 hr⁻¹, thereby giving a different weight/weight productivity value. This difference effectively prevents a direct comparison between weight/weight productivity values determined under different conditions (in this case, at a different n-butane in-air concentration and a different space velocity).

Comparison of the weight/weight productivity values obtained with catalysts 1-7, and 17-21 with those obtained with comparative catalysts 8-16 clearly demonstrates the advantages of the catalysts prepared in accordance with the instant process in that the weight/weight productivity values are significantly and consistently higher for catalysts 1-7 and 17-21 when compared with comparative catalysts 8-16. Examples 18 (1150 hr⁻¹ and 2600 hr⁻¹ in addition to 1450 hr⁻¹) and 22 (2600 hr⁻¹) also exhibits excellent weight/weight productivity.

Thus, it is apparent that there has been provided in accordance with the instant invention, a process that fully satisfies the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for the preparation of a phosphorus-vanadium mixed oxide oxidation catalyst for the production of maleic anhydride wherein the catalyst exhibits a weight/weight productivity to maleic anhydride of at least 70 g MAN/kg cat.-hr based upon a performance test conducted at a concentration of 1.5 mole percent hydrocarbon-in-air, a space velocity of 1450 hr⁻¹ under a pressure of 1.055 × 10² kPa-G, and a temperature sufficient to maintain the hydrocarbon conversion within the range of 70 mole percent to 90 mole percent, which process comprises:
   (a) introducing a substantially pentavalent vanadium-containing compound into an alcohol medium capable of reducing the vanadium to a valence state less than +5 to form a slurry;
   (b) contacting the slurry with an effective amount of alcohol-modifying agent;
   (c) effecting the reduction of at least a portion of the vanadium to a valence state of +4;
   (d) adding a pentavalent phosphorus-containing compound to the vanadium-containing mixture before or after effecting the reduction to form a phosphorus-vanadium mixed oxide catalyst precursor;
   (e) recovering the phosphorus-vanadium mixed oxide catalyst precursor;
   (f) drying the catalyst precursor; and
   (g) calcining the catalyst precursor at a temperature from about 250° C. to about 600° C.

2. The process of claim 1 wherein the alcohol medium is essentially anhydrous.

3. The process of claim 1 wherein the alcohol-modifying agent is selected from the group consisting of hydrogen iodide, sulfur dioxide, fuming sulfuric acid, and surfactants.

4. The process of claim 3 wherein the alcohol-modifying agent is sulfur dioxide.

5. The process of claim 1 wherein the alcohol modifying agent is employed in an amount sufficient to provide an alcohol-modifying agent/vanadium-containing comppound mole ratio of 1.0.

6. The process of claim 1 wherein the phosphorus-containing compound is added to the vanadium-containing mixture before effecting the reduction of the vanadium.

7. The process of claim 1 wherein the phosphorus-containing compound is added to the vanadium-containing mixture after effecting the reduction of the vanadium.

8. The process of claim 1 wherein reduction of the vanadium is effected by heating the vanadium-containing slurry under reflux conditions.

9. The process of claim 8 wherein the reflux conditions are maintained for a period ranging from about four hours to about 20 hours.

10. The process of claim 1 wherein the alcohol is isobutyl alcohol.

11. The process of claim 1 wherein the vanadium-containing compound is vanadium pentoxide.

12. The process of claim 1 wherein the phosphorus-containing compound is phosphoric acid.

13. The process of claim 12 wherein the concentration of the phosphoric acid is at least 100%.

14. The process of claim 1 wherein the catalyst precursor is recovered by filtration.

15. The process of claim 1 wherein the catalyst precursor is formed into structures.

16. The process of claim 1 wherein the catalyst precursor is calcined in an air calcination mode.

17. The process of claim 1 wherein the catalyst precursor is calcined in a nitrogen/steam calcination mode.

18. The process of claim 1 wherein the catalyst precursor calcination temperature is from about 275° C. to about 425° C.

19. The process of claim 1 wherein the catalyst has a phosphorus/vanadium atom ratio from about 0.5 to about 2.0.

20. The process of claim 19 wherein the catalyst has a phosphorus/vanadium atom ratio from about 0.95 to about 1.2.

21. The process of claim 1 wherein the catalyst has an average valence state of vanadium from about +3.9 to about +4.6.

22. The process of claim 1 wherein the catalyst has an intrinsic surface area of about 10 m$^2$/g to about 40 m$^2$/g.

23. An oxidation catalyst for the production of maleic anhydride by the partial oxidation of non-aromatic hydrocarbons comprising the mixed oxides of phosphorus and vanadium, wherein the catalyst exhibits a weight/weight productivity to maleic anhydride of at least 70 g MAN/kg cat.-hr., which catalyst is prepared by the steps comprising:
(a) introducing a substantially pentavalent vanadium-containing compound into an alcohol medium capable of reducing the vanadium to a valence state less than +5 to form a slurry;
(b) contacting the slurry with an effective amount of an alcohol-modifying agent;
(c) effecting the reduction of at least a portion of the vanadium to a valence state of +4;
(d) adding a pentavalent phosphorus-containing compound to the vanadium-containing mixture before or after effecting the reduction to form a phosphorus-vanadium mixed oxide catalyst precursor;
(e) recovering the phosphorus-vanadium mixed oxide catalyst precursor;
(f) drying the catalyst precursor; and
(g) calcining the catalyst precursor at a temperature from about 250° C. to about 600° C.

24. The process of claim 23 wherein the alcohol medium is essentially anhydrous.

25. The process of claim 23 wherein the alcohol-modifying agent is selected from the group consisting of hydrogen iodide, sulfur dioxide, fuming sulfuric acid, and surfactants.

26. The process of claim 25 wherein the alcohol-modifying agent is sulfur dioxide.

27. The process of claim 23 wherein the alcohol-modifying agent is employed in an amount sufficient to provide an alcohol-modifying agent/vanadium-containing compound mole ratio of 1.0.

28. The process of claim 23 wherein the phosphorus-containing compound is added to the vanadium-containing mixture before effecting the reduction of the vanadium.

29. The process of claim 23 wherein the phosphorus-containing compound is added to the vanadium-containing mixture after effecting the reduction of the vanadium.

30. The process of claim 23 wherein reduction of the vanadium is affected by heating the vanadium-containing slurry under reflux conditions.

31. The process of claim 30 wherein the reflux conditions are maintained for a period ranging from about four hours to about 20 hours.

32. The process of claim 23 wherein the alcohol is isobutyl alcohol.

33. The mixture of claim 23 wherein the vanadium-containing compound is vanadium pentoxide.

34. The process of claim 23 wherein the phosphorus-containing compound is phosphoric acid.

35. The process of claim 34 wherein the concentration of the phosphoric acid is at least 100%.

36. The process of claim 23 wherein the catalyst precursor is recovered by filtration.

37. The process of claim 23 wherein the catalyst precursor is formed into structures.

38. The process of claim 23 wherein the catalyst precursor is calcined in an air calcination mode.

39. The process of claim 23 wherein the catalyst precursor is calcined in a nitrogen/steam calcination mode.

40. The process of claim 23 wherein the catalyst precursor calcination temperature is from about 275° C. to about 425° C.

41. The process of claim 23 wherein the catalyst has a phosphorus/vanadium atom ratio from about 0.5 to about 2.0.

42. The process of claim 41 wherein the catalyst has a phosphorus/vanadium atom ratio from about 0.95 to about 1.2.

43. The process of claim 23 wherein the catalyst has an average valence state of vanadium from about +3.9 to about +4.6.

44. The catalyst composition of claim 23 wherein the catalyst has an intrinsic surface area of about 10 m$^2$/g to about 40 m$^2$/g.

45. An oxidation catalyst comprising the mixed oxides of phosphorus and vanadium characterized by an average valence state of vanadium from about +3.9 to about +4.6, a phosphorus/vanadium atom ratio of about 0.5 to about 2.0, and a macrostructure predominantly comprising generally spheroidal particles consisting of radially oriented three-dimensional networks of randomly shaped open cells, which catalyst is prepared by the steps comprising:
(a) introducing a substantially pentavalent vanadium-containing compound into an alcohol medium capable of reducing the vanadium to a valence state less than +5 to form a slurry;
(b) contacting the slurry with an effective amount of an alcohol-modifying agent;
(c) effecting the reduction of at least a portion of the vanadium to a valence state of +4;
(d) adding a pentavalent phosphorus-containing compound to the vanadium-containing mixture before or after effecting the reduction to form a phosphorus-vanadium mixed oxide catalyst precursor;
(e) recovering the phosphorus-vanadium mixed oxide catalyst precursor;
(f) drying the catalyst precursor; and
(g) calcining the catalyst precursor at a temperature from about 250° C. to about 600° C.

46. The process of claim 45 wherein the alcohol medium is essentially anhydrous.

47. The process of claim 45 wherein the alcohol-modifying agent is selected from the group consisting of hydrogen iodide, sulfur dioxide, fuming sulfuric acid, and surfactants.

48. The process of claim 47 wherein the alcohol-modifying agent is sulfur dioxide.

49. The process of claim 45 wherein the alcohol-modifying agent is employed in an amount sufficient to provide an alcohol-modifying agent/vanadium-containing compound mole ratio of 1.0.

50. The process of claim 45 wherein the phosphorus-containing compound is added to the vanadium-containing mixture before effecting the reduction of the vanadium.

51. The process of claim 45 wherein the phosphorus-containing compound is added to the vanadium-containing mixture after effecting the reduction of the vanadium.

52. The process of claim 45 wherein reduction of the vanadium is effected by heating the vanadium-containing slurry under reflux conditions.

53. The process of claim 52 wherein the reflux conditions are maintained for a period ranging from about four hours to about 20 hours.

54. The process of claim 45 wherein the alcohol is isobutyl alcohol.

55. The process of claim 45 wherein the vanadium-containing compound is vanadium pentoxide.

56. The process of claim 45 wherein the phosphorus-containing compound is phosphoric acid.

57. The process of claim 56 wherein the concentration of the phosphoric acid is at least 100%.

58. The process of claim 45 wherein the catalyst precursor is recovered by filtration.

59. The process of claim 45 wherein the catalyst precursor is formed into structures.

60. The process of claim 45 wherein the catalyst precursor is calcined in an air calcination mode.

61. The process of claim 45 wherein the catalyst precursor is calcined in a nitrogen/steam calcination mode.

62. The process of claim 45 wherein the catalyst exhibits a weight/weight productivity to maleic anhydride of at least 70 g MAN/kg cat.-hr.

63. The process of claim 45 wherein the catalyst has an intrinsic surface area of about 10 m²/g to about 40 m²/g.

64. A process for the preparation of a phosphorus-vanadium mixed oxide oxidation catalyst for the production of maleic anhydride wherein the catalyst exhibits a weight/weight productivity to maleic anhydride of at least 70 g MAN/kg cat.-hr based upon a performance test conducted at a concentration of 1.5 mole percent hydrocarbon-in-air, a space velocity of 1450 hr$^{-1}$ under a pressure of $1.055 \times 10^2$ kPa-G, and a temperature sufficient to maintain the hydrocarbon conversion within the range of 70 mole percent to 90 mole percent, which process comprises:
(a) introducing a substantially pentavalent vanadium-containing compound into an alcohol medium capable of reducing the vanadium to a valence state less than +5 to form a slurry;
(b) contacting the slurry with an effective amount of an alcohol-modifying agent selected from the group consisting of anionic, nonionic, zwitterionic, ampholytic surfactants, and mixtures thereof;
(c) effecting the reduction of at least a portion of the vanadium to a valence state of +4;
(d) adding a pentavalent phosphorus-containing compound to the vanadium-containing mixture before or after effecting the reduction to form a phosphorus-vanadium mixed oxide catalyst precursor;
(e) recovering the phosphorus-vanadium mixed oxide catalyst precursor;
(f) drying the catalyst precursor; and
(g) calcining the catalyst precursor at a temperature from about 250° C. to about 600° C.

65. An oxidation catalyst for the production of maleic anhydride by the partial oxidation of nonaromatic hydrocarbons comprising the mixed oxides of phosphorus and vanadium, wherein the catalyst exhibits a weight/weight productivity to maleic anhydride of at least 70 g MAN/kg cat.-hr based upon a performance test conducted at a concentration of 1.5 mole percent hydrocarbon-in-air, a space velocity of 1450 hr$^{-1}$ under a pressure of $1.055 \times 10^2$ kPa-G, and a temperature sufficient to maintain the hydrocarbon conversion within the range of 70 mole percent to 90 mole percent, which catalyst is prepared by the steps comprising:
(a) introducing a substantially pentavalent vanadium-containing compound into an alcohol medium capable of reducing the vanadium to a valence state less than +5 to form a slurry;
(b) contacting the slurry with an effective amount of an alcohol-modifying agent selected from the group consisting of anionic, nonionic, zwitterionic, ampholytic surfactants, and mixtures thereof;
(c) effecting the reduction of at least a portion of the vanadium to a valence state of +4;
(d) adding a pentavalent phosphorus-containing compound to the vanadium-containing mixture before or after effecting the reduction to form a phosphorus-vanadium mixed oxide catalyst precursor;
(e) recovering the phosphorus-vanadium mixed oxide catalyst precursor;
(f) drying the catalyst precursor; and
(g) calcining the catalyst precursor at a temperature from about 250° C. to about 600° C.

66. An oxidation catalyst comprising the mixed oxides of phosphorus and vanadium characterized by an average valence state of vanadium from about +3.9 to about +4.6, a phosphorus/vanadium atom ratio of about 0.5 to about 2.0, and a macrostructure predominantly comprising generally spheroidal particles consisting of radially oriented three-dimensional networks of randomly shaped open cells, which catalyst is prepared by the steps comprising:
- (a) introducing a substantially pentavalent vanadium-containing compound into an alcohol medium capable of reducing the vanadium to a valence state less than +5 to form a slurry;
- (b) contacting the slurry with an effective amount of an alcohol-modifying agent selected from the group consisting of anionic, nonionic, zwitterionic, ampholytic surfactants, and mixtures thereof;
- (c) effecting the reduction of at least a portion of the vanadium to a valence state of +4;
- (d) adding a pentavalent phosphorus-containing compound to the vanadium-containing mixture before or after effecting the reduction to form a phosphorus-vanadium mixed oxide catalyst precursor;
- (e) recovering the phosphorus-vanadium mixed oxide catalyst precursor;
- (f) drying the catalyst precursor; and
- (g) calcining the catalyst precursor at a temperature from about 250° C. to about 600° C.

* * * * *

UNITED STATES PATENT AND TRADEMARK OFFICE
CERTIFICATE OF CORRECTION

PATENT NO. : 4,567,158
DATED : January 28, 1986
INVENTOR(S) : James T. Wrobleski It is certified that error appears in the above-identified patent and that said Letters Patent are hereby corrected as shown below:

Column 5, line 15, delete "$H_2PO_4$" and substitute therefor -- $H_3PO_4$ --.

Column 23, line 33, delete "presents" and substitute therefor -- prevents --.

Signed and Sealed this

First Day of March, 1988

Attest:

DONALD J. QUIGG

Attesting Officer

Commissioner of Patents and Trademarks